US010034850B2

(12) United States Patent
Gerber et al.

(10) Patent No.: US 10,034,850 B2
(45) Date of Patent: Jul. 31, 2018

(54) SPRAYABLE AQUEOUS COMPOSITION COMPRISING GLYCERYL TRINITRATE

(71) Applicant: G. POHL-BOSKAMP GMBH & CO. KG, Hohenlockstedt (DE)

(72) Inventors: Andreas Gerber, Lubeck (DE); Michaela Gorath, Hamburg (DE); Thomas Zimmeck, Hohenlockstedt (DE)

(73) Assignee: G. POHL-BOSKAMP GMBH & CO. KG, Hohenlockstedt (DE)

( * ) Notice: Subject to any disclaimer, the term of this patent is extended or adjusted under 35 U.S.C. 154(b) by 0 days.

(21) Appl. No.: 15/037,691

(22) PCT Filed: Nov. 28, 2014

(86) PCT No.: PCT/EP2014/076020
§ 371 (c)(1),
(2) Date: May 19, 2016

(87) PCT Pub. No.: WO2015/079049
PCT Pub. Date: Jun. 4, 2015

(65) Prior Publication Data
US 2016/0296488 A1 Oct. 13, 2016

(30) Foreign Application Priority Data
Nov. 29, 2013 (EP) .................... 13005562

(51) Int. Cl.
*A61K 31/21* (2006.01)
*A61K 9/08* (2006.01)
*A61K 47/32* (2006.01)
*A61K 47/34* (2017.01)
*A61K 9/00* (2006.01)
*A61K 47/10* (2017.01)
*A61K 47/26* (2006.01)

(52) U.S. Cl.
CPC .............. *A61K 31/21* (2013.01); *A61K 9/006* (2013.01); *A61K 9/0014* (2013.01); *A61K 9/08* (2013.01); *A61K 47/10* (2013.01); *A61K 47/26* (2013.01); *A61K 47/32* (2013.01); *A61K 47/34* (2013.01)

(58) Field of Classification Search
None
See application file for complete search history.

(56) References Cited

U.S. PATENT DOCUMENTS

| 3,155,574 | A | 11/1964 | Silson et al. |
|---|---|---|---|
| 4,323,577 | A | 4/1982 | Ohkuma et al. |
| 4,542,013 | A | 9/1985 | Keith |
| 4,919,919 | A | 4/1990 | Aouda et al. |
| 5,047,230 | A | 9/1991 | Nagy et al. |
| 5,186,925 | A | 2/1993 | Cholcha |
| 5,370,862 | A | 12/1994 | Klokkers-Bethke et al. |
| 5,698,589 | A | 12/1997 | Allen |
| 5,744,124 | A | 4/1998 | Klokkers-Bethke et al. |
| 5,989,529 | A | 11/1999 | Kaplan |
| 6,443,307 | B1 | 9/2002 | Burridge |
| 6,962,691 | B1 | 11/2005 | Lulla et al. |
| 7,781,226 | B2 | 8/2010 | McDevitt et al. |
| 7,872,049 | B2 | 1/2011 | Groteluschen et al. |
| 8,147,872 | B2 | 4/2012 | Crew et al. |
| 2002/0032232 | A1 | 3/2002 | Bing |
| 2003/0026849 | A1 | 2/2003 | Thomas |
| 2003/0078517 | A1 | 4/2003 | Kensey |
| 2003/0095925 | A1 | 5/2003 | Dugger, III |
| 2004/0213744 | A1 | 10/2004 | Lulla et al. |
| 2004/0228883 | A1 | 11/2004 | Karl |
| 2005/0191620 | A1 | 9/2005 | McDevitt et al. |
| 2005/0192210 | A1 | 9/2005 | Rothbard et al. |
| 2006/0003011 | A1 | 1/2006 | Crew et al. |
| 2007/0053966 | A1 | 3/2007 | Ang et al. |
| 2007/0059346 | A1 | 3/2007 | Maibach |
| 2008/0260861 | A1 | 10/2008 | Hagendoorn et al. |
| 2009/0221540 | A1 | 9/2009 | Bennink |
| 2010/0016446 | A1 | 1/2010 | Gonda et al. |
| 2010/0184870 | A1 | 7/2010 | Groteluschen et al. |
| 2010/0216893 | A1 | 8/2010 | Groteluschen et al. |
| 2010/0227922 | A1 | 9/2010 | Groteluschen et al. |
| 2011/0002987 | A1 | 1/2011 | Poli et al. |
| 2011/0240508 | A1 | 10/2011 | Groteluschen et al. |
| 2012/0237567 | A1 | 9/2012 | Hagendoorn et al. |

FOREIGN PATENT DOCUMENTS

| CA | 2718345 A1 | 9/2009 |
|---|---|---|
| CN | 101229148 A | 7/2008 |
| DE | 3246081 A1 | 6/1984 |
| DE | 3922650 A1 | 1/1990 |

(Continued)

OTHER PUBLICATIONS

Xylitol, Handbook of Pharmaceutical Excipients, Sixth Edition, 2009, Editors: Rowe et al., pp. 786-789.*
Database WPI, XP002662296 & RU 2174838C2, IVAN MED ACAD, Week 200202, Thomson Scientific, [2001] Abstract.
Database Caplus [Online], Chemical Abstracts Service, Columbus, Ohio, US, 2004, Chen, Baoxi et al: "Effect of acrylonitrile-butadiene rubber on nitroglycerin migration from propellant to EPDM inhibitor", retrieved from STN, Database accession No. 2004:826842, Abstract.
Sergio H. Ferreira et al., "Blockade of hyperalgesia and neurogenic oedema by topical application of nitroglycerin," European Journal of Pharmacology, 1992, vol. 217, pp. 207-209.
Johns Hopkins Sports Medicine Patient Guide to Muscle Strain; date unavailable; Johns Hopkins Medicine, Orthopaedic Surgery [online], [retrieved Jan. 20, 2015], Retrieved from the Internet: <URL: http://www.hopkinsortho.org/muscle_strain.html>.

(Continued)

*Primary Examiner* — Savitha M Rao
*Assistant Examiner* — Gregg Polansky
(74) *Attorney, Agent, or Firm* — K&L Gates LLP

(57) ABSTRACT

The present application relates to a pharmaceutical preparation comprising (a) from 0.15 to 3 weight percent of glyceryl trinitrate, (b) from 40 to 95 weight percent water, and (c1) from 2 to 10 weight percent of at least one water soluble polymer, or (c2) from 1 to 10 weight percent of at least one water soluble polymer and 5 to 20 weight percent of ethanol.

9 Claims, 31 Drawing Sheets

(56) References Cited

FOREIGN PATENT DOCUMENTS

Figure 1:
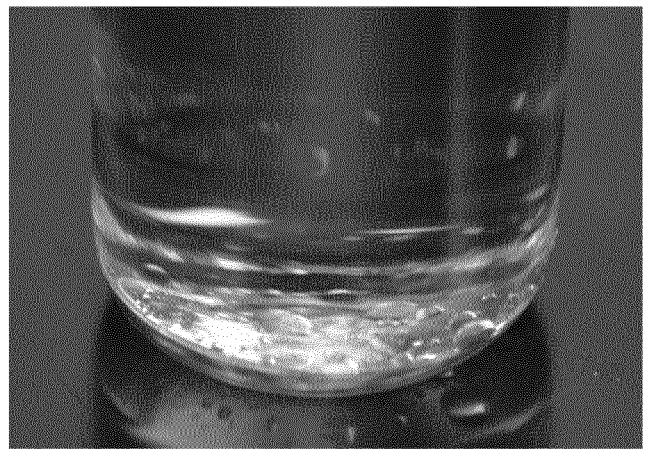

| | | |
|---|---|---|
| DE | 4038203 A1 | 6/1992 |
| DE | 202008007318 U1 | 7/2008 |
| DE | 102008005484 A1 | 7/2009 |
| EP | 0448961 A2 | 10/1991 |
| EP | 0461505 A1 | 12/1991 |
| EP | 0471161 A1 | 2/1992 |
| EP | 1004294 A1 | 5/2000 |
| GB | 1205019 A | 9/1970 |
| RU | 2174838 C2 | 10/2001 |
| WO | 82/00005 A1 | 1/1982 |
| WO | 88/05306 A1 | 7/1988 |
| WO | 96/27372 A1 | 9/1996 |
| WO | 97/38687 A1 | 10/1997 |
| WO | 99/17766 A1 | 4/1999 |
| WO | 99/38472 A2 | 8/1999 |
| WO | 01/43735 A1 | 6/2001 |
| WO | 01/68062 A2 | 9/2001 |
| WO | 03/066472 A1 | 8/2003 |
| WO | 2004064779 A2 | 8/2004 |
| WO | 2005/004989 A1 | 1/2005 |
| WO | 2005107461 A2 | 11/2005 |
| WO | 2007/123955 A2 | 11/2007 |
| WO | 2008105731 A1 | 9/2008 |
| WO | 2009/092358 A1 | 7/2009 |
| WO | 11/02606 A1 | 1/2011 |

OTHER PUBLICATIONS

Definition of Bruise; 1996-2015, last editorial review Mar. 19, 2012; MedicineNet [online], [retrieved Jan. 20, 2015] Retrieved from the Internet: <URL: http://www.medicinenet.com/script/main/art.asp?articlekey=2541>.

Edema, Dictionary.com [online], [retrieved Jun. 18, 2015] Retrieved from the Internet; <URL:http://dictionary.reference.com/browse/edema>.

Fernandes et al., "Nitric oxide-induced inhibition of mouse paw edema: involvement of soluble guanylate cyclase and potassium channels," Inflammation Research, 2002, vol. 51, pp. 377-384.

Zegarska et al., "Clinical and experimental aspects of cutaneous neurogenic inflammation" Pharmacological Reports, [2006], vol. 58, pp. 13-21.

Molecularinfo.com reference [Retrieved on Dec. 1, 2010 from the Internet: <URL: http://www.molecularinfo.com/MTM/D/D3/D3-r/D3-4-60.html], 1 pg.

Nitrolingual Pumpspray product insert (nitroglycerin lingual spray), G. Pohl-Boskamp GmbH & Co. KG, Oct. 2008, 4 pgs.

Nitrolingual Pumpspray package labelling (nitroglycerin lingual spray), G. Pohl Boskamp GmbH & Co. KG, Nov. 2008, 1 pg.

Nitrolingual Pumpspray bottle labelling (nitroglycerin lingual spray), G. Pohl-Boskamp GmbH & Co. KG, May 2006, 2 pgs.

Scheife et al., Journal of Pharmaceutical Sciences, vol. 71, Issue 1, Abstract, 1982, 1 pg.

Schranz et al., (1981), "Hemorrhagic pulmonary edema and cardiac failure following isolated head injury. Treatment with dobutamine and nitroglycerin," Monatsschr Kinderheilkd, 129 (4): 248-250. Abstract.

Kuroda et al., (1997), "Changes in cerebral blood flow accompanied with reduction of blood pressure treatment in patients with hypertensive intracerebral hemorrhages," Neurol Res., 19(2): 169-73. Abstract.

International Search Report for International Application No. PCT/EP2011/003890, dated Nov. 11, 2011. 6 pages.

Written Opinion for International Application No. PCT/EP2011/003890, dated Nov. 11, 2011. 9 pages.

Fernandes et al., (2004), "Involvement of guanylate cyclase and potassium channels on the delayed phase of mouse carrageenan-induced paw edema," European Journal of Pharmacology, Elsevier Science, NL, vol. 501, No. 1-3, pp. 209-214.

Bel Trame et al., (1998) "Nitrate therapy is an alternative to furosemidel morphine therapy in the management of acute cardiogenic pulmonary edema," Journal of Cardiac Failure, vol. 4, No. 4, pp. 271-279.

International Search Report for International Application No. PCT/EP2009/001772, dated Jun. 16, 2009. 3 pages.

Written Opinion for International Application No. PCT/EP2009/001772, dated Jun. 16, 2009. 4 pages.

International Search Report for International Application No. PCT/EP2012/000803, dated Jun. 25, 2012. 4 pages.

Written Opinion for International Application No. PCT/EP2012/000803, dated Jun. 25, 2012. 7 pages.

M. J. Pikal et al: "Vapor pressure of nitroglycerin in sublingual molded tablets: Implications for stability", Journal of Pharmaceutical Sciences, 1976, vol. 65, No. 9, pp. 1278-1284.

M. J. Pikal et al: "Polymer sorption of nitroglycerin and stability of molded nitroglycerin tablets in unit-dose packaging", Journal of Pharmaceutical Sciences, 1977, vol. 66, No. 9, pp. 1293-1297.

M. J. Pikal et al: "Effect of nitroglycerin-soluble additives on the stability of molded nitroglycerin tablets", Journal of Pharmaceutical Sciences, 1984, vol. 73, No. 11, pp. 1608-1612.

"Glyceryl Monostearate", In: R C Rowe. P J Sheskey. S C Owen: "Handbook of Pharmaceutical Excipients, 5th Edition", 2005, Pharmaceutical Press, London.

International Search Report for International Application No. PCT/EP2012/000802, dated Jun. 6, 2012. 4 pages.

Written Opinion for International Application No. PCT/EP2012/000802, dated Jun. 6, 2012. 6 pages.

"Barex Resins", INEOS Barex, USA, 2006, Retrieved from the Internet: URL:http://www.ineosbarex.com/files/upload/Ineos%20Barex%20Brochure.pdf, retrieved on May 15, 2012, the whole document.

Daniel Banes: "Deterioration of nitroglycerin tablets", Journal of Pharmaceutical Sciences, vol. 57, No. 5, 1968, pp. 893-894.

European Search Report for EP12004187, Date of completion of search Sep. 28, 2012.

Cui X, et al., "Role of endothelial nitric oxide synthetase in arteriogenesis after stroke in mice", Neuroscience, New York, NY, US, vol. 159, No. 2, 2009, pp. 744-750.

Dinesh Kumar, et al., "Chronic sodium nitrite therapy augments ischemia-induced angiogenesis and arteriogenesis", Proceedings of the National Academy of Sciences, National Academy of Sciences, US, vol. 105, No. 21, 2008, pp. 7540-7545.

Hopkins et al., "Controlled delivery of vascular endothelial growth factor promotes neovascularization and maintains limb function in a rabbit model of ischemia", Journal of Vascular Surgery, C.V. Mosby CO., ST Louis, MO, US, vol. 27, No. 5, 1998, pp. 886-895.

Persson et al., "Therapeutic arteriogenesis in peripheral arterial disease: Combining Intervention and Passive Training", Vasa Journal for Vascular Diseases, vol. 40, No. 3, 2011, pp. 177-187.

Sager H.B. et al., "Temporal patterns of blood flow and nitric oxide synthase expression affect macrophage accumulation and proliferation during collateral growth", J Angiogenes Res, 2010, vol. 2, No. 18, pp. 1-11.

Troidl K., et al., "Effects of Endogenous Nitric Oxide and of DETA NONOate in Arteriogenesis", J Cardiovsc Pharmacol, 2010, vol. 55, No. 2, pp. 153-160.

Troidl K. and Schaper W, "Arteriogenesis versus angiogenesis in peripheral artery disease", Diabetes/Metabolism Research and Reviews, 2012, vol. 28, S1, pp. 27-29.

D. J. Danziger et al. "Automated site-directed drug design: a general algorithm for knowledge acquisition about hydrogen-bonding regions at protein surfaces" Proc. R. Soc. Lond. B, [1989], vol. 236, pp. 101-113.

Svend Aage Schou "Stability and Stabilization of Pharmaceutical Preparations" Pharmaceutica acta Helvetiae, [1959], vol. 34, No. 8/9, pp. 309-330.

Barry A. Edelman et al. "The Stability of Hypodermic Tablets of Nitroglycerin Packaged in Dispensing Containers" Journal of the American Pharmaceutical Association, NS11, [1971], pp. 30-33.

International Search Report from PCT/EP2014/076020 dated Feb. 23, 2015.

* cited by examiner

10 DAYS RIP PBS:

10 DAYS SHAM PBS:

5 DAYS RIP PBS:

5 DAYS SHAM PBS:

5 DAYS SHAM NTG-PLACEBO:

5 DAYS SHAM NTG:

5 DAYS RIP NTG-PLACEBO:

5 DAYS RIP NTG:

5 DAYS RIP ISDN-PLACEBO:

5 DAYS RIP ISDN:

5 DAYS RIP ASA + PBS:

5 DAYS RIP ASA + NTG-PLACEBO:

5 DAYS RIP ASA + NTG:

SPRAYABLE AQUEOUS COMPOSITION COMPRISING GLYCERYL TRINITRATE

This is the national phase under 35 U.S.C. § 371 of International Application No. PCT/EP2014/076020, filed on Nov. 28, 2014, which claims priority to and the benefit of EP Application No. 13005562.7, filed on Nov. 29, 2013, the entire contents of each of which are incorporated herein by reference.

The invention concerns pharmaceutical preparations with the active substance glyceryl trinitrate in the form of an aqueous solution comprising a water soluble polymer, the use of the pharmaceutical preparation, a process for the preparation of the pharmaceutical preparation and a kit comprising the pharmaceutical preparation.

Glyceryl trinitrate (nitroglycerin, abbr. GTN) is a pharmaceutical active substance that is used among others for treating angina pectoris attacks. It is especially useful in emergency situations, when the pharmaceutical form must guarantee a quick onset of action. Sublingual sprays have proven highly efficacious because spraying the formulation into the mouth represents a direct and quick procedure to apply the dose onto a great part of the mucosa. GTN is quickly absorbed from the mucosa and can act within seconds.

GTN containing sprays may be formulated with or without the addition of a propellant. Propellant sprays are disclosed for example in the U.S. Pat. No. 3,155,574, in the European patent application EP 0 461 505 and the German application DE 32 460 81. A GTN containing formulation without propellant for use as a pump spray is described in the European patent application EP 0 448 961.

GTN is a medium polarity liquid with limited water solubility, but it dissolves easily in a plurality of other solvents. Spray formulations may also be based on non-aqueous lipophilic, on non-aqueous solvents that are miscible with water or on solvent systems containing water. For example, the patent EP 0 448 961 describes a rather lipophilic preparation with a preferred content of triglycerides of 80% and ethanol as a co-solvent in a concentration of 20%. The propellant spray according to the teaching of patent application EP 0 927 032 that contains approximately 30% triglycerides beside the propellant can also be characterized as highly lipophilic. In contrast, the propellant spray according to U.S. Pat. No. 3,155,574 with 25% ethanol belongs to the second group of formulations. Also DE 3 922 650 A1 discloses a propellant free spray formulation that contains no water: GTN is dissolved in a plurality of polar solvents. In the European patent application EP 0 471 161 a pump spray is described that contains ethanol, 1,2-propandiol and 42% water as solvents. The concentration of marketed GTN sprays is usually below 1%, because the therapeutically effective dose for treating an angina pectoris attack lies below 1 mg.

The solubility of nitroglycerin in water is about 1 mg/ml. In the European patent EP 0 108 248B1 solutions of GTN in a concentration range of 0.08 to 0.11 weight percent are proposed for infusion. This low concentration is sufficient for a solution for intravenous infusion to achieve therapeutic effects, because a comparatively large volume of the solution can be applied. For a topical pharmaceutical form however, this is not true. When a volume of more than 100 µl is applied sublingually, there is a remarkable risk of swallowing the drug. The active substance is resorbed from the gastrointestinal tract much more slowly than through the oral mucosa and the blood concentration is further decreased by a prominent first-pass effect. Therefore the necessary plasma levels for a rapid and effective treatment in an emergency situation can not be reached in this way. In a similar manner there is also an upper limit for dermal application of a spray solution, because when larger amounts, e.g. more than 100 µl, are applied they may get lost by dripping or running away. To reach efficacious plasma levels the concentration of the active substance in a topical GTN containing solution needs to be higher than 1 mg/ml, for example not less than 1.5 mg/ml.

U.S. Pat. No. 5,698,589 describes a topical cream with a GTN concentration between 0.2 and 1.5 weight percent. The active substance is formulated in an emulsion. This galenic form is not appropriate for sublingual or oral application because of difficulties of dosing and patient compliance. In general, such preparations are not sprayable because of their high viscosity. Consequently, they can not be sprayed onto the skin or into the oral cavity. The patient would have to remove it from its container, put it for example onto a finger and then apply it onto the skin or the oral mucosa. Therefore a topical cream is not appropriate. Moreover, emulsions contain emulsifiers and other excipients for topical application that may not be acceptable for oral preparations because of their bad taste or toxicological properties. Finally the active substance needs to be released from the emulsion, before it can be absorbed. This release is hindered because of the content of oily or greasy components in the oil phase of the emulsion and thickeners in the water phase. This aspect is also a severe drawback for the dermal application.

Taken together a considerable need for sprayable GTN preparations remains. They should be well tolerated after topical application and guarantee a sufficient uptake of the active substance into the body. The preparations should be easy to manufacture and to apply.

The object of the present invention is to deliver a stable pharmaceutical preparation in the form of an aqueous solution containing not less than 0.15 weight percent of GTN.

This object is solved by a pharmaceutical preparation comprising:

(a) from 0.15 to 3 weight percent of glyceryl trinitrate,
(b) from 40 to 95 weight percent water, and
(c1) from 2 to 10 weight percent of at least one water soluble polymer,
or
(c2) from 1 to 10 weight percent of at least one water soluble polymer and 5 to 20 weight percent of ethanol.

According to the present invention, the term "weight percent" always refers to the weight of the pharmaceutical preparation. In other words, a pharmaceutical preparation according to the invention always comprises 100 weight percent.

In the context of the present invention, it has been surprisingly found that by the use of water soluble polymers the active substance GTN stays in solution without an intolerable increase of viscosity of the solution which would e.g. compromise sprayability of a sprayable embodiment of the invention. Therefore, such a pharmaceutical preparation characterized by low viscosity as defined herein can be prepared when, apart from usual excipients, a least one water soluble polymer is present that ameliorates the well-documented and typical insolubility of the active substance, GTN. This is illustrated by representative GTN-containing preparations described in Examples 1 to 4 herein. The findings documented herein stand contrary to approaches heretofore utilized by formulation chemists working to prepare improved, clinically-useful GTN-containing liquids. First, the water content of the present invention is substantially above that currently understood to be possible when working with GTN. Second, the combination of high water content and a water-soluble polymer resulting in a clinically- and commercially-useful GTN-containing aqueous formulation is unexpected in view of the state of the art. And, third, the viscous properties of the present invention being compatible with a sprayable embodiment of the present invention are also unexpected.

"Low viscosity" in the context of this invention means that the viscosity measured at 20° C. with a rotational viscosimeter at a shear rate of 1800/s is not more than 50 mPa*s; in a preferred embodiment it is not more than 40 mPa*s, most preferred not more than 30 mPa*s.

"Water soluble" in the sense of this invention means that the solubility of the polymers in water at 20° C. is not less than 0.5 weight percent, preferably not less than 1 weight percent and most preferably not less than 2 weight percent relative to the total composition. The solubility is measured by stirring the respective amount of polymer in 100 ml water for 24 h and then visually judging the clarity of the solution.

"Stable" in the sense of this invention means both physical and chemical stability: The pharmaceutical preparation preferably remains homogeneous during storage at elevated temperatures (up to 50° C.) and when refrigerated (5° C.), it preferably shows no relevant loss of the active component when stored at 25° C. for two years. In especially preferred embodiments, the preparation can be frozen at −20° C. and results in a clear solution after thawing and shaking of the container.

The pharmaceutical preparation of the present invention comprises 0.15 to 3 weight percent of GTN.

The concentration of GTN is preferably in the range from 0.15 to 2 weight percent, most preferred are concentrations of 0.2, 0.25, 0.3, 0.4, 0.5, 0.6, 0.7, 0.8, 1.0, 1.2 and 1.5 weight percent.

Because of its explosive properties GTN for use in drug products is preferably phlegmatised by the GTN producer. "Phlegmatised" means it is incorporated in a matrix reducing the dangerous characteristics. Both liquid and solid compounds may be used as phlegmatisers. For example GTN can be purchased as a 5% solution in propylene glycol, as a 10% trituration in lactose monohydrate or in 2.25% dilution in glucose. When these concentrated GTN containing products are used directly for producing preparations according to the invention the phlegmatisers are also present in the pharmaceutical preparation. A preferred embodiment of the invention uses GTN in propylene glycol. Most preferably, a 5% solution of GTN in propylene glycol is used.

The pharmaceutical preparation according to this invention comprises from 40 to 95 weight percent water. Preferably, the pharmaceutical preparation comprises from 60 to 90 weight percent of water. Preferred water contents are 60, 65, 70, 75, 80, 85, 90, and 95 weight percents.

The pharmaceutical preparation comprises at least one water soluble polymer.

The water-soluble polymer is preferably a non-ionic water soluble polymer.

In a preferred embodiment, the water soluble polymer is selected from the group consisting of tyloxapol and poloxamer.

Tyloxapol is a non-ionic alkyl aryl polyether alcohol comprising the following formula (I):

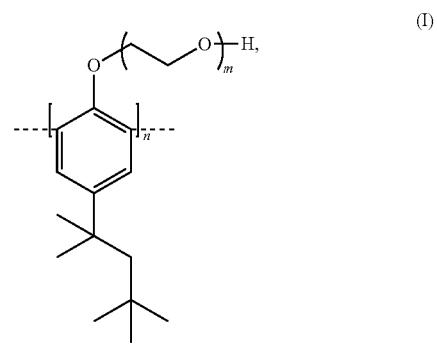

wherein m is preferably from 6 to 8 and n is preferably less than 6. Tyloxapol is available from e.g. Pressure Chemicals, Pittsburgh, Pa., United States of America.

Poloxamer is a copolymer of ethylene oxide and propylene oxide and comprises the following formula (II):

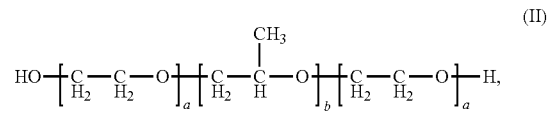

wherein a and b are preferably as defined below.

The poloxamer may be poloxamer 124, poloxamer 188, poloxamer 237, poloxamer 338 or poloxamer 407.

In poloxamer 124, a is from 10 to 15 and b is from 18 to 23. The content of oxyethylene is 44.8% to 48.6% and the average relative molecular mass is 2090 to 2360.

In poloxamer 188, a is from 75 to 85 and b is from 25 to 30. The content of oxyethylene is 79.9% to 83.7% and the average relative molecular mass is 7680 to 9510.

In poloxamer 237, a is from 60 to 68 and b is from 35 to 40. The content of oxyethylene is 70.5% to 74.3% and the average relative molecular mass is 6840 to 8830.

In poloxamer 338, a is from 137 to 146 and b is from 42 to 47. The content of oxyethylene is 81.4% to 84.9% and the average relative molecular mass is 12700 to 17400.

In poloxamer 407, a is from 95 to 105 and b is from 54 to 60. The content of oxyethylene is 71.5% to 74.9% and the average relative molecular mass is 9840 to 14600.

Poloxamer 407 is available e.g. under the trademark Kolliphor® P407 from BASF, Ludwigshafen, Germany.

In a preferred embodiment the water soluble polymer is tyloxapol.

In a further preferred embodiment the water soluble polymer is poloxamer 407.

In a further preferred embodiment the water soluble polymer is a mixture of tyloxapol and at least one poloxamer.

The water soluble polymer is used in a concentration between 2 and 10 weight percent, for example in a concentration of 2, 2.5, 3, 4, 5, 6, 7, 8, 9 or 10 weight percent. The concentration is chosen as low as possible, because with increasing amount of polymer the viscosity of the preparation increases in a disproportionate manner.

The invention also encompasses a pharmaceutical preparation comprising from 1.0 to 10 weight percent of at least one water soluble polymer and 5 to 20 weight percent of ethanol. The water soluble polymer is, for example in a concentration of 1, 1.5, 2, 3, 4, 5, 6, 7, 8, 9 or 10 weight percent and ethanol is preferably in a concentration of 10, 12, 15, 18 or 20 weight percent.

In preferred embodiments, the pharmaceutical preparation comprises:
- from 1 to 5 weight percent of at least one water soluble polymer and 10 to 20 weight percent of ethanol,
- from 2 to 4 weight percent of at least one water soluble polymer and 12 to 18 weight percent of ethanol, or
- from 2 to 3 weight percent of at least one water soluble polymer and 15 weight percent of ethanol.

The pharmaceutical preparations according to the invention may additionally comprise other pharmaceutically acceptable excipients. The pharmaceutically acceptable excipient may be at least one additive selected from the group consisting of preservatives, taste components, flavour components, sweeteners, acids and bases to adjust the pH and buffering substances.

In an embodiment of the invention, the pharmaceutical preparation comprises from 0 to 50 weight percent of at least one additive. In a preferred embodiment, the pharmaceutical preparation comprises from 30 to 50 weight percent of at least one additive. In a more preferred embodiment, the pharmaceutical preparation comprises from 30 to 45 weight percent of at least one additive.

In a further preferred embodiment of the invention, the pharmaceutical preparation comprises from 0 to 1 weight percent of at least one additive as defined above.

In one preferred embodiment the pharmaceutical preparation comprises the sugar alcohol xylitol as taste component.

It is desirable that the preparation causes a significant taste perception in the patient to make him sure that e.g. the spray jet has been actuated correctly and has hit the target area e.g. below the tongue. Xylitol is a "tooth friendly" sugar replacement. Hence, it is appropriate to use it in the pharmaceutical preparation for causing the desired taste sensation.

In a preferred embodiment, the pharmaceutical preparation may be applied as a spray jet that may be as small as 50 µl. Therefore, comparatively high concentrations of xylitol would be necessary. Preferred concentrations of xylitol in the pharmaceutical preparation are therefore in the range of 5 to 50 weight percent, more preferred from 30 to 45 weight percent.

The pharmaceutical preparation may additionally comprise at least one preservative. Preservatives prevent the microbial deterioration of the pharmaceutical preparation. They may be used in concentrations from 0.01 to 1 weight percent. Examples are benzoic acid, sorbic acid and the methyl, ethyl and propyl ester of 4-hydroxybenzoic acid. Beside these preservatives ethanol can also be used as a preservative. The necessary amount of ethanol is in the range of 5 to 20 weight percent, preferably from 10 to 20 weight percent.

In an embodiment of the invention, the pharmaceutical preparation does not comprise ethanol.

The stability of GTN in aqueous solution exhibits an optimum in the weakly acidic pH range. Therefore the buffering substance that optionally may be present in the preparation according to this invention shall be chosen from the group of substances that possess a good buffering capacity, preferably in the pH range from 3.0 to 7.0.

In a preferred embodiment of the present invention, these buffering substances are organic acids and their physiologically acceptable salts or inorganic acids and their physiologically acceptable salts. Examples of buffering substances are lactic acid/sodium lactate, citric acid/sodium citrate, gluconic acid/sodium gluconate, phosphoric acid/dibasic and monobasic potassium phosphate. The buffer concentration is preferably chosen in a way that prevents pH shifts in the course of a two-years storage at 25° C. of more than 0.5 pH units. Preferably it is between 0.1 and 1 weight percent.

In another preferred embodiment, the pharmaceutical preparation further comprises propylene glycol. The amount of propylene glycol can be in the range from 0 to 40 weight percent.

The viscosity of the pharmaceutical preparation is preferably ≤50 mPa*s and more preferably ≤30 mPa*s.

In a further aspect of the invention, the pharmaceutical preparation is used in a method for the prevention or treatment of an arterial insufficiency.

According to the present invention, the term "treatment" or "prevention" means that not only symptoms of the disease are relieved but that also the disease itself is treated or prevented. In a preferred embodiment, the term "treatment" means improving the prognosis of said disease.

According to the invention, the term "arterial insufficiency" refers to any insufficient blood or oxygen supply or any other insufficient supply of a tissue which is provided by an artery. This insufficient supply can be overcome by the methods and uses of the present invention wherein a pharmaceutical composition is used to increase the supply of a given tissue. The arterial insufficiency may occur both during physical rest and during an exercise.

In a preferred embodiment of the present invention, the arterial insufficiency is due to insufficient oxygen or blood supply of a tissue supplied by the artery or a bypass or shunt during physical rest or exercise.

According to a further preferred embodiment, the arterial insufficiency is due to an increased demand of oxygen or blood flow of a tissue supplied by the artery or a bypass or shunt.

This increased demand of oxygen or blood flow can have several reasons including but not limited to increased sport or physical activity, and increased mental activity or a disease requiring an increased demand of oxygen or blood flow.

According to a further preferred embodiment, the arterial insufficiency is characterized by a partial (stenosis) or complete occlusion of an arterial vessel. In the context of the present invention, the term "partial occlusion" is equivalent to a stenosis.

The partial or complete occlusion of an arterial vessel is a well-known phenomenon. It can have various reasons including, but not limited to, deposition of material in the blood vessels (including non-revascularisable stenoses), compression from external tissue or fluid next to the vessel (including disturbance in diastolic myocardial relaxation), vascular spasm, dysfunction of the endothelium of the vessel resulting in a paradoxic vasoconstriction during exercise or microvascular impairment due to endothelial dysfunction or smooth muscle cell abnormalities.

In a preferred embodiment, the arterial insufficiency is due to the deposition of material in the blood vessels.

The deposition of materials in the blood vessels is a well-known phenomenon resulting e.g. in atherosclerosis.

In a further preferred embodiment, the arterial insufficiency is due to an external or internal compression of an artery.

An internal compression of an artery may be due to an edema but also to a tumor putting pressure on the artery. Furthermore, this includes a vasospastical constriction of the artery as e.g. in Prinzmetal's angina. In addition, this also includes the paradoxic vasoconstriction which e.g. sometimes occur in an endothelial dysfunction or constricted small arterial vessels due to endothelial or smooth muscle cell dysfunction.

An external compression may be due to an accident or any external force which can put pressure on an artery.

In a further preferred embodiment, the arterial insufficiency is a vascular disease.

According to a further preferred embodiment, the arterial insufficiency is a disease selected from the group consisting of atherosclerosis, an ischemic disease and a further chronic arterial disease.

In a further preferred embodiment, the arterial insufficiency is a coronary arterial insufficiency.

In a preferred embodiment, the coronary insufficiency is an atherosclerotic coronary arterial insufficiency, in particular coronary artery disease (coronary heart disease or ischemic heart disease), stable angina pectoris, unstable angina pectoris, myocardial ischemia or chronic myocardial ischemia, acute coronary syndrome, myocardial infarction (heart attack or ischemic myocardial infarction), or ischemia-induced heart failure.

In a further preferred embodiment, the coronary insufficiency is a non-atherosclerotic, in particular coronary microvascular disease (small vessel disease) or cardiac syndrome X, or Prinzmetal's angina.

In a further preferred embodiment, the arterial insufficiency is a cerebral arterial insufficiency (intra- or extracranial).

In a preferred embodiment, the cerebral arterial insufficiency is an atherosclerotic cerebral arterial insufficiency, in particular cerebral ischemia, extracranial carotid artery disease, extracranial vertebral artery disease, transient ischemic attack (mini stroke or pre-stroke), stroke, vascular dementia, ischemic brain diseases, or ischemic cerebrovascular disease.

The cerebral arterial insufficiency may also be ischemic microvascular brain disease, small vessel vascular dementia, subcortical arteriosclerotic encephalopathy (Binswanger's disease), Alzheimer's disease, or Parkinson's disease.

In a preferred embodiment, the arterial insufficiency is a peripheral arterial insufficiency.

In a preferred embodiment, the peripheral arterial insufficiency is an atherosclerotic peripheral arterial insufficiency, in particular peripheral vascular disease (peripheral artery disease (PAD) or peripheral artery occlusive disease (PAOD), including lower and upper extremity arterial disease), walking impairment or limited walking distance, claudication or intermittent claudication, ischemic limb symptoms including pain, weakness, numbness or cramping in muscles due to decreased blood flow, ischemic rest pain, abnormal ankle brachial pressure index, ischemic limb lesions (skin color changes, skin dryness, slowly or non-healing wounds or ulcers, necrosis, gangrene), chronic critical limb ischemia, or the need for limb amputation.

In a preferred embodiment, the peripheral arterial insufficiency is a non-atherosclerotic peripheral arterial insufficiency, in particular Raynaud's syndrome (vasospasmatic), thrombangiitis obliterans (endangitis obliterans or Buerger's disease; recurring progressive inflammation and thrombosis (clotting) of small and medium arteries and veins of the hands and feet), vascular inflammatory disease (vasculitis), or compartment syndromes.

In a preferred embodiment, the arterial insufficiency is induced by diabetes, in particular diabetic ischemia disorders, including diabetic ischemic foot syndrome, diabetic neuropathy, diabetic retinopathy and maculopathy, or diabetic macular edema.

In a further preferred embodiment, the arterial insufficiency may be an intestinal arterial insufficiency, in particular an atherosclerotic intestinal arterial insufficiency, in particular ischemic bowel disease, mesenteric ischemia, or mesenteric infarction.

In a further preferred embodiment, the arterial insufficiency may be an urogenital arterial insufficiency, in particular an atherosclerotic urogenital arterial insufficiency, in particular erectile dysfunction, renal artery disease, renal ischemia, or renal infarction.

In a further preferred embodiment, the arterial insufficiency may be a nerval arterial insufficiency, in particular tinnitus or diabetic neuropathy.

Furthermore, the arterial insufficiency may be in the context of scleroderma (systemic sclerosis).

Furthermore, the arterial insufficiency may be in the context of fibromuscular dysplasia.

In a preferred embodiment, the arterial insufficiency is a central retinal artery insufficiency, in particular an atherosclerotic central retinal artery insufficiency, in particular ocular arterial insufficiency.

In a further preferred embodiment, the arterial insufficiency is characterized by an absence of an endothelial dysfunction.

The endothelial dysfunction is a well-known systemic pathological state of the endothelium and can be broadly defined as an imbalance between vasodilating and vasoconstricting substances produced by or acting on the endothelium.

In a further preferred embodiment, the arterial insufficiency is a chronic arterial insufficiency. In the context of the present invention, the term "chronic arterial insufficiency" means that the course of the arterial insufficiency is chronic and often progredient.

According to a further embodiment, the chronic arterial insufficiency includes endothelial dysfunction, atherosclerosis, coronary artery disease (coronary heart disease or ischemic heart disease), stable angina pectoris, coronary microvascular disease (small vessel disease) or cardiac syndrome X, Prinzmetal's angina, vascular dementia, ischemic brain diseases, or ischemic cerebrovascular disease, ischemic microvascular brain disease, small vessel vascular dementia, subcortical atherosclerotic encephalopathy (Binswanger's disease), Alzheimer's disease, Parkinson's disease, peripheral vascular disease (peripheral artery disease (PAD) or peripheral artery occlusive disease (PAOD), thrombangiitis obliterans (endangiitis obliterans or Buerger's disease), vascular inflammatory disease (vasculitis), fibromuscular dysplasia, diabetic ischemic disorders, diabetic neuropathy, ischemic bowel disease, erectile dysfunction, renal artery disease, tinnitus, and scleroderma (systemic sclerosis).

In a preferred embodiment, the arterial insufficiency is a disease and/or its symptom selected from the group consisting of atherosclerosis, endothelial dysfunction, microvascular dysfunction, vasospastic disease, an ischemic disease, a further acute or chronic arterial disease, a microvessel disease, an intestinal arterial insufficiency, an urogenital arterial insufficiency, a nerval arterial insufficiency, scleroderma, or a central retinal artery insufficiency.

In a further preferred embodiment, the arterial insufficiency is a coronary arterial insufficiency preferably selected from the group consisting of coronary artery disease (coronary heart disease), ischemic heart disease, stable and unstable angina pectoris, acute coronary syndrome, myocardial ischemia, myocardial infarction, ischemia-induced heart failure, coronary microvascular disease (small vessel disease) or cardiac syndrome X, coronary spasms or Prinzmetal's angina.

In a further preferred embodiment, the arterial insufficiency is an intra- or extracranial cerebral arterial insufficiency preferably selected from the group consisting of cerebral ischemia, extracranial carotid artery disease, extracranial vertebral artery disease, transient ischemic attack (mini-stroke or pre-stroke), stroke, vascular dementia, ischemic brain diseases, or ischemic cerebrovascular disease.

In a most preferred embodiment, the arterial insufficiency is a peripheral arterial insufficiency, preferably selected from the group consisting of Raynaud's syndrome, diabetic ischemia disorders, including diabetic ischemic foot syndrome or diabetic neuropathy, thromboangiitis obliterans (endangiitis obliterans or Buerger's disease), vascular inflammatory disease (vasculitis), compartment syndromes, peripheral artery disease (peripheral artery occlusive disease), walking impairment or limited walking distance, claudication or intermittent claudication, ischemic limb symptoms (pain, weakness, numbness or cramping in muscles due to decreased blood flow), ischemic rest pain, abnormal ankle brachial pressure index, ischemic limb lesions (skin color change, skin dryness, slowly or non-healing wounds or ulcers, necrosis, gangrene), chronic critical limb ischemia, or the need for limb amputation.

The pharmaceutical preparation according to the present invention is particularly suitable for promoting collateral circulation. This might be explained by the short-term dilatation of the collateral vessel induced by the pharmaceutical preparation which, in turn, has a significantly improved effect on arteriogenesis. An arteriogenesis e.g. can function as a good prophylaxis of tissue ischemia in general or of severe disease associated events as e.g. myocardial infarction, stroke, ischemic heart failure, such as post-infarction heart failure, or limb amputation in the case of peripheral artery disease. Arteriogenesis can have a positive influence on the prognosis of the disease and prevent progredient disease development.

According to the invention, the pharmaceutical preparation is administered in an amount capable of inducing arteriogenesis. The skilled person will appreciate that this amount will depend on the subject to which the pharmaceutical preparation is administered. Generally, the amount of active substance to be administered may be from 0.05 to 50 mg per day, but this can vary due to the weight of the subject, its hemodynamic response to the pharmaceutical preparation and/or the severity of the disease.

The amount to be administered can also vary depending on the way of administration. E.g. when administered sublingually, inhalatively, or bucally the preferred amount of GTN can be from 0.1 to 8 mg per day. E.g. when administered dermally, the preferred amount can be 0.1 to 30 mg Hence, the amount of the pharmaceutical preparation to be administered may be from 0.1 to 15 ml per day, or, alternatively, from 0.02 to 3 ml per day, dependent on the nature of the pharmaceutical preparation and/or its way of administration.

In a preferred embodiment, an amount of 0.05 to 1.6 mg GTN may be administered per single application lingually, sublingually, bucally or oromucosally. This amount may be administered 1- up to 5-times maximally, resulting in a maximal dosage of active substance of 8 mg per day.

In a preferred embodiment, an amount of 0.025 to 1.0 ml (0.025, 0.05, 0.1, 0.2, 0.3, 0.5, 0.75, 1.0) of the pharmaceutical preparation is applied for at least 1- up to maximal 5-times daily, resulting in a maximal dosage of active substance of 3.2 mg per day.

According to the invention, the term "administration of the pharmaceutical preparation" means that a given dosage of the pharmaceutical preparation is administered. Depending on the way of administration, the skilled person will appreciate that the administration may take some time. In a preferred embodiment, the pharmaceutical preparation is administered in form of a spray, sprayable or injectable solution, or inhalable aerosol, which means that the administration may be completed within seconds. However, the administration of the pharmaceutical preparation may also take longer, e.g. if the pharmaceutical preparation is administered to the patient by way of infusion. Modes of administration of the pharmaceutical preparation are further discussed below.

Furthermore, according to the invention, the pharmaceutical preparation is administered in a manner capable of inducing arteriogenesis.

The inventors of the present invention have surprisingly found out that a pharmaceutical preparation according to the invention is capable of inducing arteriogenesis when administered in an intermitting manner.

According to the invention, the term "intermitting manner" means that the pharmaceutical preparation is administered in a way that its plasma or tissue levels are only elevated in a short-term manner after the administration of the pharmaceutical preparation but then again decline. This can be achieved for example if the pharmaceutical preparation has a composition as defined above and the administration of the pharmaceutical preparation is followed by a time period without administration and then the pharmaceutical preparation is again administered to the subject. Furthermore, this way of administration avoids that the subject is developing tolerances against the pharmaceutical preparation and that the subject is developing endothelial dysfunction.

The induction of endothelial dysfunction is a parameter which has a prognostic significance in patients with coronary artery disease. The development of tolerances as well as the induction of endothelial dysfunction are well known disadvantages caused by the sustained, long term exposure to NO donors (Uxa A. et al., Journal of Cardiovascular Pharmacology, 2010, 56 (4): 354-359).

Moreover, the administration of a pharmaceutical preparation according to the invention in an intermitting manner has the effect that it mimics the physiological situation of the organism as, for example, comparable to the endogenous release of NO upon physical training. In other words, the pharmaceutical preparation of the present invention acts as a biomimetic when applied in an intermitting manner.

In a preferred embodiment, the plasma or tissue levels of the active compound of the pharmaceutical preparation are elevated for not more that 240, 180, 120, or 60 minutes, or for not more than 50, 40, 30, 15, 10 or 5 minutes.

Furthermore, this also implies that the pharmaceutical preparation can be administered in chronic manner, i.e. without taking account of disease developments implying an acute treatment with the pharmaceutical preparation. Furthermore, it also implies that a therapy plan can be established without taking account of disease developments implying an acute treatment with the pharmaceutical preparation.

The pharmaceutical preparation is used to achieve a relief or acute (i.e. immediate) prevention of the symptoms of a corresponding disease. These symptoms for example include pain and/or dyspnea in the case of a cardiovascular disease, and the relief or acute prevention of the symptoms was achieved by vasodilation and resulting pain and/or dyspnea relief.

In the context of the present invention, the term "intermittently" also means that the pharmaceutical preparation is not administered continuously, for example by means of long term intravenous infusion or with the help of an implanted pump which constantly delivers the pharmaceutical preparation to the subject. Rather, this term also means that there is an interval between two administrations of the pharmaceutical preparation, and that the pharmaceutical preparation is given several times, e.g. at least 1, 2, 3, 4, 5, 6, 8, 9, 12 or 16 times a day.

As the skilled person will appreciate, one administration of the pharmaceutical preparation may include an administration in one or more dosage forms, e.g. hubs (puffs) in case of a spray. For example, one administration may include the administration of one to three hubs (puffs).

As to the schedule of administration, the skilled person will appreciate that there are many ways to achieve this intermitting administration. For example, it is possible to administer the pharmaceutical preparation at least once a day and at least on one day a week for at least two weeks. However, it is equally possible to administer the pharmaceutical preparation for only one week if the pharmaceutical preparation is administered several times during this week.

Preferable, the pharmaceutical preparation is administered once, twice or three times a day, wherein even more preferred the time period between two administrations of the pharmaceutical preparation is at least 4 hours, in particular 8 hours, in particular at least 10 hours or 12 hours.

Although possible, it is not necessary that the time periods between two administrations of the pharmaceutical preparations are the same. Rather, it is preferred that these time periods differ, depending on the individual administration schedule.

In an embodiment, the pharmaceutical preparation is administered at least on one day a week. However, the pharmaceutical preparation may also be administered on 2, 3, 4, 5, 6 or 7 days a week. In an especially preferred embodiment, the pharmaceutical preparation is administered at least on 3 or 4 days a week.

According to the invention, it is possible to administer the pharmaceutical preparation for a period of several weeks or months. This is particularly preferred in order to induce arteriogenesis efficiently, although also a shorter administration of one of two weeks is possible.

In an embodiment, the pharmaceutical preparation is administered for 2 to 8 weeks. It is equally preferred to administer the pharmaceutical preparation for 3 to 6, 3 to 8, 3 to 10 or 4 to 8, 4 to 10 or 4 to 12 weeks. These numbers are only examples and may vary depending on the individual schedule of the subject.

In an embodiment, the pharmaceutical preparation is taken at least once a week for at least 8 weeks, in particular for at least 12 weeks.

In a further preferred embodiment, the pharmaceutical preparation is taken not longer than 6, 8 or 12 months. However, it is also possible to take the pharmaceutical preparation for 2, 3 or even more years. Furthermore, it is also possible that the pharmaceutical preparation is administered for decades or even through the whole life of the subject.

In the context of such long-term administrations, it is preferred that the pharmaceutical preparation is administered once or twice a week or at least once or twice a week.

It has been described previously that an exogenous stimulation of pulsatile shear forces in an individual may result in arteriogenesis. Furthermore, it has been described how the pulsatile shear forces can be measured (WO 2010/072416).

Consequently, in a preferred embodiment, the pharmaceutical preparation is administered in conjunction with an exogenous stimulation of the pulsatile shear forces in the artery.

In a further preferred embodiment, the pharmaceutical preparation is administered when the subject is at rest.

With respect to said embodiment of the invention, the pharmaceutical preparation should be administered in a way that it is active in the body of the subject when the exogenous stimulation is applied. In this context, active means that either the NO release is not yet terminated or the NO released from the active substance GTN is still present and active. Depending on the physiological halftime of the active substance in the subject and its formulation, the skilled person will be capable of determining when the pharmaceutical preparation has to be administered to the subject in order to ensure that it is active upon the exogenous stimulation.

In the case of GTN, the halftime and its persistence in the body of the subject has been intensively studied, e.g. after intravenous or sublingual application, where it is 2 to 5 minutes in the blood plasma, see e.g. Armstrong P. W. et al., Circulation, 1979, 59: 585-588 or Armstrong P. W. et al., Circulation, 1980, 62:160-166.

In general, the halftime of GTN in the blood plasma is 2 to 5 minutes.

It is to be understood that, in the context of the present invention, the term "halftime" refers to the half-life and/or to the half-life time of the GTN in the subject's body, in particular in the subject's blood plasma.

In an embodiment, the pharmaceutical preparation is administered in the time period of 30 minutes before the onset of the exogenous stimulation until 30 minutes after the termination of the exogenous stimulation.

More preferably, the pharmaceutical preparation is administered in the time period of 15 minutes, preferably 5 minutes, more preferably 2 minutes before the exogenous stimulation until 30, preferably 15, more preferably 5 minutes after the onset of the exogenous stimulation.

In a further preferred embodiment, the pharmaceutical preparation is administered once a day, five times a week for 6 weeks 2-5 minutes before the exogenous stimulation.

The exogenous stimulation of the pulsatile shear forces may be achieved by any known way. This includes an stimulation with the help of medicaments like medicaments which increase the blood pressure.

In a preferred embodiment, said stimulation is achieved by physical exercise or the application of an endogenous force to the arterial vessel.

According to the invention, the term "physical exercise" means any training of the subject, including but not limited to training in exercise rooms, jogging, walking, nordic walking, swimming, dancing, cycling and hiking. The skilled person will appreciate that any exercise will be helpful in the context of the invention, provided that it is performed in conjunction with the administration of the pharmaceutical preparation. Preferably, the term "physical exercise" does not include unsupervised, unprescribed routine movements like casual walking or house work.

As discussed above, it has been found in the context of the present invention that the pharmaceutical preparation is capable of inducing arteriogenesis. This enables not only the treatment of an already existing disease. Rather, in the context of the present invention, it is also possible to prevent the disease. Consequently, in a preferred embodiment of the present invention, the method aims at the prevention of said arterial insufficiency.

In the context of the present invention, it has been possible to reduce the infarct size in case of an already existing occlusion. Furthermore, it has been possible to reduce arrhythmias in the subjects. Consequently, in a preferred embodiment of the present invention, the method results in a reduction of the infarct size, in reduced arrhythmias or in a decreased ST segment elevation.

The pharmaceutical preparation can be administered in any suitable way so that it can be incorporated into the subject. This includes an oral, parenteral or intravenous administration as well as the injection of the pharmaceutical preparation into the body of the subject, but also an administration to a mucous membrane or the skin of the subject.

In a most preferred embodiment of the present invention, the pharmaceutical preparation is administered orally or sublingually.

In a preferred embodiment of the present invention, the pharmaceutical preparation is administered topically, lingually, sublingually, inhalatively, bucally, mucosally, transmucosally or oromucosally, dermally or cutaneously, transdermally or percutaneously.

The term "mucosally" according to the present invention means that the pharmaceutical preparation is applied on the mucosa.

The term "transmucosally" according to the present invention means that the pharmaceutical preparation, especially the active substance, passes the mucosa.

The term "oromucosally" according to the present invention means that the pharmaceutical preparation, especially the active substance, is applied in the oral cavity and/or the throat.

The terms "dermally" and "cutaneously" as well as "transdermally" and "percutaneously" can be used interchangeably in the present invention.

In case of a lingual, sublingual or oromucosal administration, it is preferred that the pharmaceutical preparation is administered with the help of a spray, sprayable or injectable solution, or by an inhalator device, from which the pharmaceutical preparation can be easily inhaled and adsorbed. It is equally preferred that the pharmaceutical preparation is administered in the form of an inhalable gas, or aerosol.

The pharmaceutical preparation can be formulated in any suitable way for the above mentioned administration modes. Such formulations are known to the person skilled in the art and include the formulation in suitable buffers or as an aerosol.

In a preferred embodiment, the pharmaceutical preparation is formulated in a way that allows a fast release of the active substance from the formulation. This includes e.g. formulations which do not hold back the active substance for a longer time period, but which release the active substance within e.g. 45, 30 or 15, 10, 5 minutes or 1 minute.

Through the invention, it is preferred that the subject to which the pharmaceutical preparation is applied is a human subject.

In a further aspect, the present invention also relates to a pharmaceutical preparation for use in a method for the prevention or treatment of an arterial insufficiency, wherein the pharmaceutical preparation is administered in an amount and manner effective for the induction of arteriogenesis.

All features and preferred embodiments discussed above for the method of treating or preventing an arterial insufficiency also apply to the pharmaceutical preparation for use according to this aspect of the invention.

In another aspect, the present invention also relates to a method of the suppression of negative effects associated with any treatment of an arterial insufficiency which is anti-arteriogenic or inhibiting arteriogenesis, comprising administering to a subject subjected to said treatment a pharmaceutical preparation in an amount and manner effective for the induction of arteriogenesis.

In a preferred embodiment, said treatment is an acetyl salicylic acid (ASA), glycoproteinIIbIIIa antagonists, or etanercept (soluble tumor necrosis factor alpha receptor) treatment.

It is known in the art that ASA is an inhibitor of arteriogenesis (Singer E. et al., Vasa, 2006, 35 (3): 174-177). Consequently, the ASA treatment of cardiovascular diseases, although being a standard therapy, has significant side effects and disadvantages. In the context of the present invention, it has been found that the pharmaceutical preparations are capable of overcoming the negative effects associated with an ASA treatment (see example section). Based on these findings, the inventors conclude that also the negative side effects associated with other medications like glycoproteinIIbIIIa antagonists or etanercept treatment can also be diminished.

Furthermore, the present invention also relates to a pharmaceutical preparation for use in a method of the suppression of negative effects associated with any treatment of an arterial insufficiency which is anti-arteriogenic or inhibiting arteriogenesis, wherein the pharmaceutical preparation is administered to a subject subjected to said treatment in an amount and manner effective for the induction of arteriogenesis.

In a preferred embodiment, said treatment is an acetyl salicylic acid (ASA), glycoproteinIIbIIIa antagonists, or etanercept (soluble tumor necrosis factor alpha receptor) treatment.

All features and preferred embodiments discussed above for the method of treating or preventing an arterial insufficiency also apply to the method for the suppression of negative effects according to this aspect of the invention or to said pharmaceutical preparation for use according to this aspect of the invention.

In a further aspect, the present invention also relates to a method for the prevention or treatment of a cardiac arrhythmia, wherein a pharmaceutical preparation according to the invention is administered to a subject in an amount and manner effective for the treatment of said cardiac arrhythmia. Furthermore, the present invention also relates to a pharmaceutical preparation for use in a method for the prevention or treatment of a cardiac arrhythmia, wherein the pharmaceutical preparation is administered to a subject in an amount and manner effective for the treatment of said cardiac arrhythmia.

In the context of the present invention, the inventors have found that pharmaceutical preparations according to the invention are capable to prevent and treat arrhythmias.

All features and embodiments defined above with respect to the pharmaceutical preparation and its formulation and administration also apply to this method or pharmaceutical preparation for use according to the invention.

The present invention also relates to a method of promoting collateral circulation comprising the step of exposing a subject to a therapeutically effective amount of a pharmaceutical preparation according to the invention wherein the therapeutically effective amount of the pharmaceutical preparation promotes arteriogenesis sufficient to augment collateral circulation in a physiological or pathological condition.

The term collateral circulation describes the circulation of blood through so-called collateral vessels. These vessels are small arterioles, which are part of a network that interconnects perfusion territories of arterial branches. In the case that the main artery itself is not capable of sufficiently supplying a tissue, e.g. due to an arterial occlusion, these collateral vessels are recruited and can develop to large conductance arteries, to bypass the site of an arterial occlusion and/or to compensate blood flow to ischemic territories supplied by the or insufficient artery. In the context of the present invention, the promotion of collateral circulation occurs via arteriogenesis.

According to the invention, the term "physiological condition" denotes any condition of the subject which is not related to any disease.

According to the invention, the term "pathological condition" denotes any condition of the subject which is related to a disease.

Preferably, the subject suffers from an arterial insufficiency.

All features and preferred embodiments discussed above for the method of treating or preventing an arterial insufficiency also apply to the method of promoting collateral circulation.

With respect to the aspects defined above where the pharmaceutical preparation is administered in a manner sufficient to induce arteriogenesis this manner is preferably an intermitting manner as defined above.

Another aspect of the present invention is a process for the preparation of a pharmaceutical preparation, comprising admixing components (a) and (c1) in water or admixing components (a) and (c2) in water.

The production process of the pharmaceutical preparations according to this invention is straight forward. Generally all water soluble compounds are dissolved in water, whereby it may be appropriate to dissolve the water soluble polymer in a separate first step. Then the GTN, preferably in the form of a concentrate, is added and the mixture is stirred vigorously until a homogeneous solution is formed.

Another aspect of the present invention is a kit comprising the pharmaceutical preparation according to the invention, wherein the kit is a spray. This kit may consist of container and spray pump. The container may be a glass or plastic bottle.

Preferred embodiments of the pharmaceutical preparations and of preparing the same are:

In a first embodiment 2 to 5 weight percent of poloxamer 407 are dissolved in water. Then 4 to 12 weight percent GTN in propylene glycol (5%) are added and stirred for 15 minutes. Optionally a mixture of 0.02% of propyl 4-hydroxybenzoate and 0.08% of methyl 4-hydroxybenzoate is added.

In a second embodiment 30 to 50 weight percent of xylitol and 2 to 5 weight percent of poloxamer 407 are dissolved in water. Then 4 to 12 weight percent GTN in propylene glycol (5%) are added and stirred for 15 minutes. Optionally a mixture of 0.02% of propyl 4-hydroxybenzoate and 0.08% of methyl 4-hydroxybenzoate is added.

In another embodiment 30 to 50 weight percent of xylitol and 1.5 to 5 weight percent of tyloxapol are dissolved in water. Then 4 to 12 weight percent GTN in propylene glycol (5%) are added and stirred for 15 minutes. Optionally a mixture of 0.02% of propyl 4-hydroxybenzoate and 0.08% of methyl 4-hydroxybenzoate is added.

In yet another embodiment 30 to 50 weight percent of xylitol, 1 to 5 weight percent of tyloxapol and 1 to 5 weight percent of poloxamer 407 are dissolved in water. Then 4 to 12 weight percent GTN in propylene glycol (5%) are added and stirred for 15 minutes. Optionally a mixture of 0.02% of propyl 4-hydroxybenzoate and 0.08% of methyl 4-hydroxybenzoate is added.

In one embodiment 30 to 50 weight percent of xylitol and 1 to 5 weight percent of poloxamer 407 are dissolved in water. Then 4 to 12 weight percent GTN in propylene glycol (5%) are diluted in 10 to 20 weight percent ethanol. Both solutions are combined and stirred for 15 minutes. Alternatively, the xylitol can be omitted.

A similar preparation free of propylene glycol can be achieved by dissolving 30 to 50 weight percent of xylitol and 1 to 5 weight percent of poloxamer 407 in water, adding 4 to 12 weight percent GTN in ethanol (5%) and 8 to 16 weight percent ethanol, and stirring for 15 minutes.

In a further embodiment 2 to 10 weight percent of poloxamer 407 are dissolved in water. Then 4 to 12 weight percent GTN in propylene glycol (5%) are added and stirred for 15 minutes. Optionally a mixture of 0.02% of propyl 4-hydroxybenzoate and 0.08% of methyl 4-hydroxybenzoate or 0.1% benzoic acid as preservative is added.

In another embodiment 30 to 50 weight percent of xylitol and 2 to 10 weight percent of poloxamer 407 are dissolved in water. Then 4 to 12 weight percent GTN in propylene glycol (5%) are added and stirred for 15 minutes. Optionally a mixture of 0.02% of propyl 4-hydroxybenzoate and 0.08% of methyl 4-hydroxybenzoate or 0.1% benzoic acid as preservative is added.

In an embodiment 1.5 to 7 weight percent of tyloxapol are dissolved in water. Then 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s) are added and the mixture is stirred for 15 minutes.

In another embodiment 30 to 50 weight percent of xylitol and 1.5 to 7 weight percent of tyloxapol are dissolved in water. Then 4 to 12 weight percent GTN in propylene glycol (5%) are added and stirred for 15 minutes. Optionally a mixture of 0.02% of propyl 4-hydroxybenzoate and 0.08% of methyl 4-hydroxybenzoate or 0.1% benzoic acid as preservative(s) is added.

In a further embodiment 1 to 5 weight percent of tyloxapol and 1 to 10 weight percent of poloxamer 407 are dissolved in water. Then 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s) are added and the mixture is stirred for 15 minutes.

In yet another embodiment 30 to 50 weight percent of xylitol, 1 to 5 weight percent of tyloxapol and 1 to 10 weight percent of poloxamer 407 are dissolved in water. Then 4 to 12 weight percent GTN in propylene glycol (5%) are added and stirred for 15 minutes. Optionally a mixture of 0.02% of propyl 4-hydroxybenzoate and 0.08% of methyl 4-hydroxybenzoate or 0.1% benzoic acid as preservative(s) is added.

In general, formulas containing xylitol are more appropriate for oral or sublingual application, whereas those not containing any sugar alcohol are better for dermal application.

A first embodiment comprises 2 to 5 weight percent of poloxamer 407 dissolved in water, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

A second embodiment comprises 2 to 5 weight percent of poloxamer 407 dissolved in water, 30 to 50 weight percent of xylitol, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

Another embodiment comprises 1.5 to 5 weight percent of tyloxapol dissolved in water, 30 to 50 weight percent of xylitol, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

Yet another embodiment comprises 1 to 5 weight percent of tyloxapol and 1 to 5 weight percent of poloxamer 407 dissolved in water, 30 to 50 weight percent of xylitol, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

Further embodiments comprise 1 to 5 weight percent of poloxamer 407 dissolved in water, 30 to 50 weight percent of xylitol, 4 to 12 weight percent GTN in propylene glycol (5%) and 10 to 20 weight percent ethanol. Alternatively, the xylitol can be omitted.

A further embodiment comprises 2 to 10 weight percent of poloxamer 407 dissolved in water, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

Another embodiment comprises 2 to 10 weight percent of poloxamer 407 dissolved in water, 30 to 50 weight percent of xylitol, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

An embodiment comprises 1.5 to 7 weight percent of tyloxapol dissolved in water, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

Another embodiment comprises 1.5 to 7 weight percent of tyloxapol dissolved in water, 30 to 50 weight percent of xylitol, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

A further embodiment comprises 1 to 5 weight percent of tyloxapol and 1 to 10 weight percent of poloxamer 407 dissolved in water, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

Yet another embodiment comprises 1 to 5 weight percent of tyloxapol and 1 to 10 weight percent of poloxamer 407 dissolved in water, 30 to 50 weight percent of xylitol, 4 to 12 weight percent GTN in propylene glycol (5%) and optionally a mixture of 0.02% of propyl 4-hydroxybenzoate and 0.08% of methyl 4-hydroxybenzoate or 0.1% benzoic acid as preservative(s).

Further embodiments comprise 1 to 5 weight percent of poloxamer 407 dissolved in water, 30 to 50 weight percent of xylitol, 4 to 12 weight percent GTN in propylene glycol (5%) and 10 to 20 weight percent ethanol. Alternatively, the xylitol can be omitted.

Embodiments free of propylene glycol comprise 30 to 50 weight percent of xylitol and 1 to 5 weight percent of poloxamer 407 dissolved in water, 4 to 12 weight percent GTN in ethanol (5%) and 8 to 16 weight percent ethanol. Also in these embodiments xylitol can be omitted preferably when the preparation is designed for a dermal application.

The invention is further described by the attached figures and examples, which are intended to illustrate, but not to limit the invention.

SHORT DESCRIPTION OF THE FIGURES

FIG. 1: Beaker comprising a composition according to comparative example 1.

Figure 2:
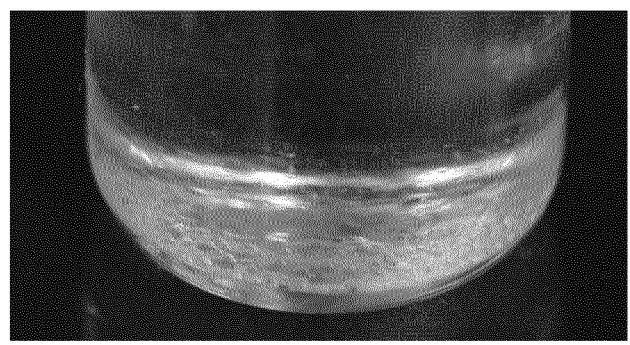

FIG. 2: Beaker comprising a composition according to comparative example 3.

Figure 3:
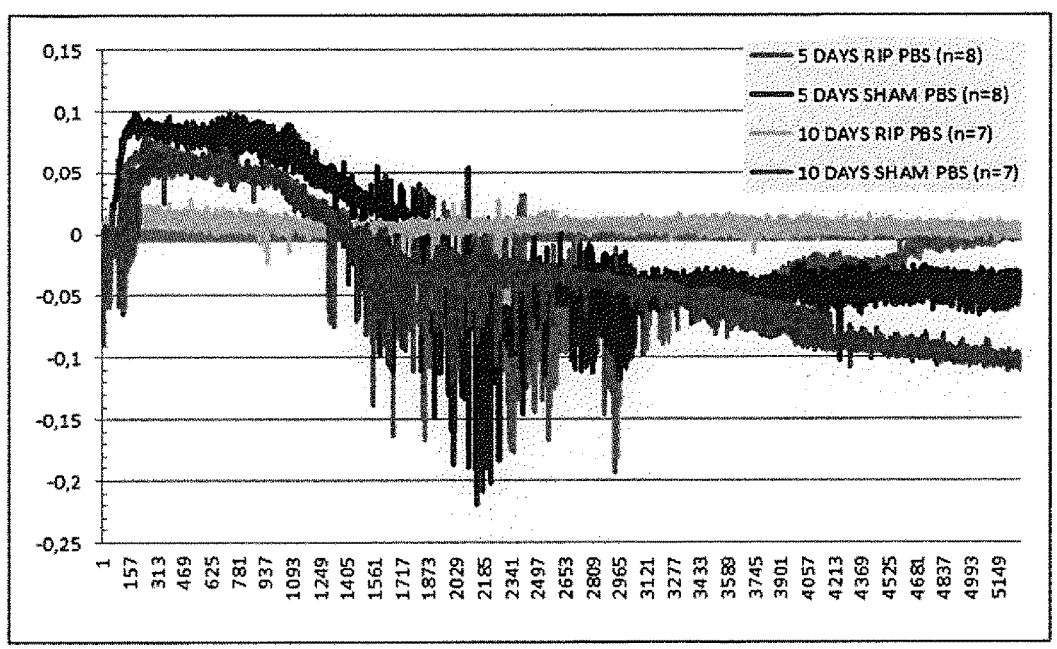

FIG. 3: Course of the ST segment elevation per beat after FPO (=final occlusion to induce infarct) of 5- and 10-days-control-groups. ECG graph in middle grey indicates 5 DAYS RIP PBS, n=8: 0.104±0.016 mV; ECG graph in black indicates 5 DAYS SHAM PBS, n=8: 0.134±0.034 mV; ECG graph in light grey indicates 10 DAYS RIP PBS, n=7: 0.055±0.033 mV; ECG graph in dark grey indicates 10 DAYS SHAM PBS, n=7: 0.124±0.039 mV.

ECG was recorded 90 minutes after FPO. Course of the ST segment elevation per beat at first 1200 beats revealed no differences between 5- and 10-days-sham-groups and 5-days-RIP-group. Only in the 10-days-RIP-group a lower ST segment elevation was observed.

Figure 4:
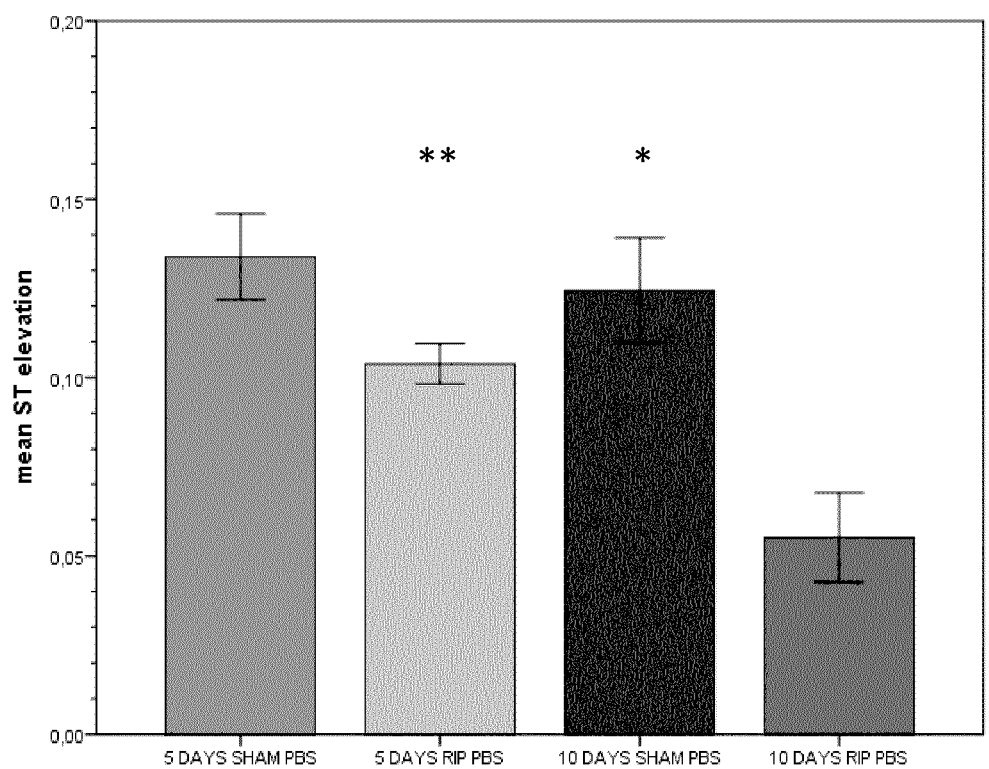

FIG. 4: ST segment elevation of 5- and 10-days-control-groups. Column 1 shows ST segment elevation of 5 DAYS SHAM PBS group; column 2 shows ST segment elevation of 5 DAYS RIP PBS group; column 3 shows ST segment elevation of 10 DAYS SHAM PBS group; column 4 shows ST segment elevation of 10 DAYS RIP PBS group; standard deviation is indicated in error bars; asterisk indicates significant compared to 10 DAYS SHAM PBS (nominal p value<0.025); double asterisk indicates significant compared to 5 DAYS RIP PBS (nominal p value<0.025).

Diagram shows mean of ST segment elevation maximum per group. After 5 days there was no significant difference found between RIP and SHAM. After 10 days in the RIP group ST segment elevation maximum was significantly lower compared to sham (*) and 5-day RIP control (**) (*, **nominal p-value<0.025).

Figure 5:
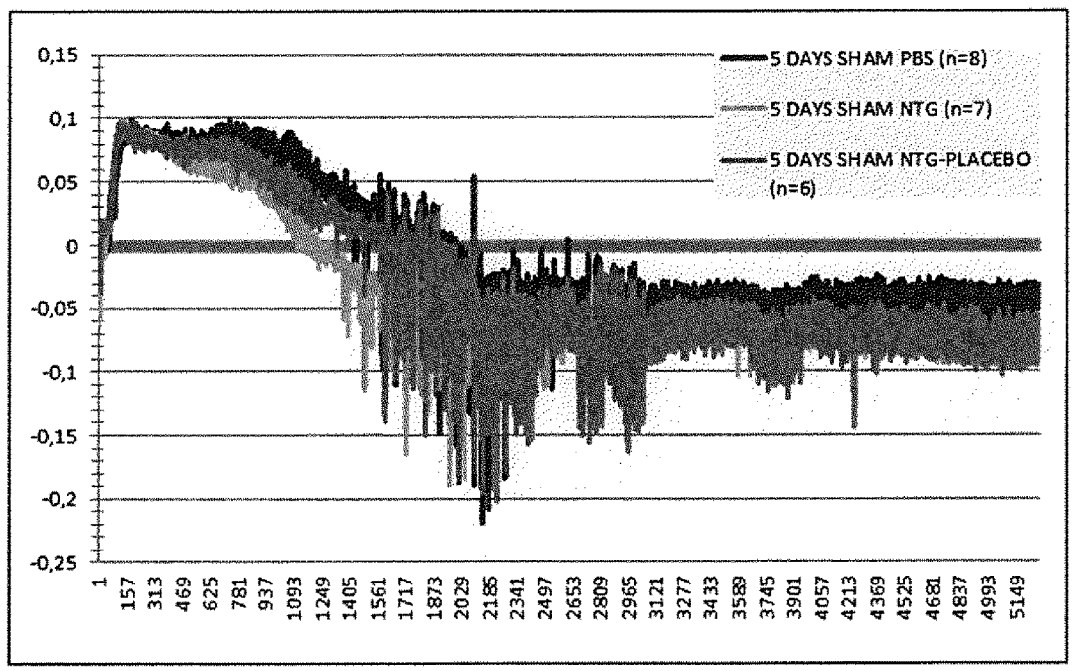

FIG. 5: Course of the ST segment elevation per beat after FPO (module 1: Sham operation without the RIP). ECG graph in black indicates 5 DAYS SHAM PBS, n=8: 0.134±0.034 mV; ECG graph in light grey indicates 5 DAYS SHAM NTG, n=7: 0.124±0.058 mV; ECG graph in middle grey indicates 5 DAYS SHAM NTG-PLACEBO, n=6: 0.131±0.043 mV.

The course of the ST segment elevation per beat after FPO revealed no differences between sham control and treated groups after 5 days.

Figure 6:
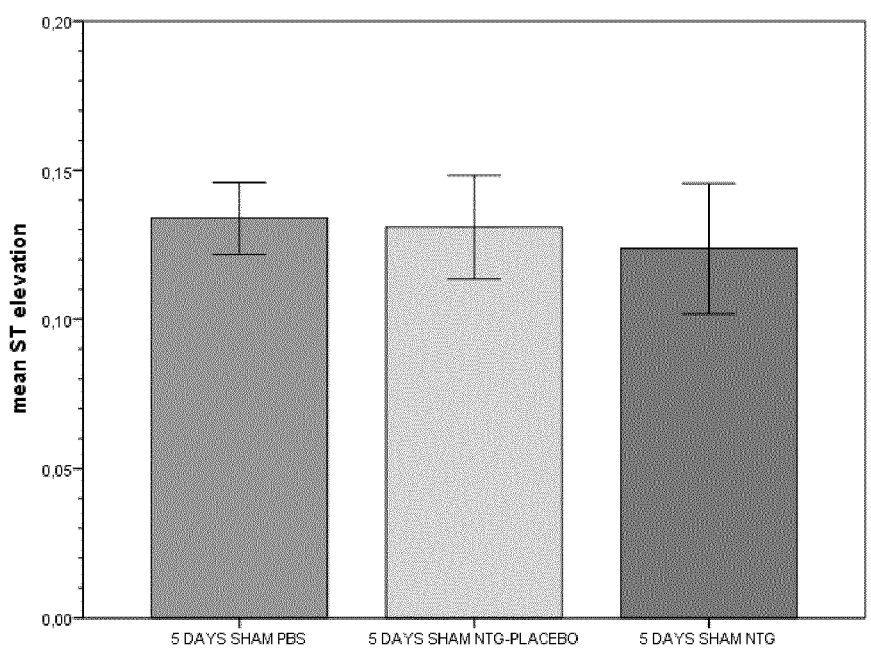

FIG. 6: ST segment elevation (module 1: Sham operation without the RIP). Column 1 shows 5 DAYS SHAM PBS; column 2 shows 5 DAYS SHAM NTG-Placebo; column 3 shows 5 DAYS SHAM NTG; standard deviation is indicated by error bars.

Diagram shows mean of ST segment elevation maximum per group. No difference in ST segment elevation maximum was found between sham control and treated groups.

Figure 7:
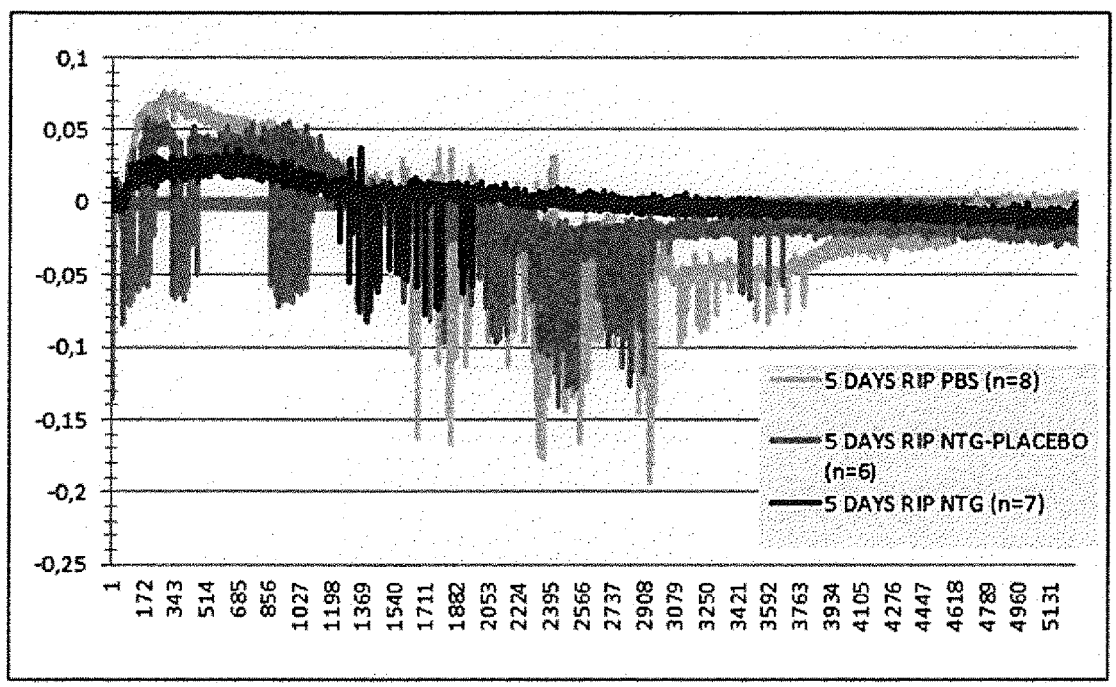

FIG. 7: Course of the ST segment elevation per beat after FPO (module 2: NO intermittent (NTG)). ECG graph in light grey indicates 5 DAYS RIP PBS, n=8: 0.104±0.016 mV; ECG graph in middle grey indicates 5 DAYS NTG-PLACEBO, n=6: 0.096±0.061 mV; ECG graph in black indicates 5 DAYS RIP NTG, n=7: 0.052±0.030 mV.

Compared to control treatment with PBS or NTG-Placebo a lower ST segment elevation course was detected after NTG treatment 5 days after RIP.

In the NTG group ("5 DAYS RIP NTG") ST segment elevation is significantly decreased compared to the PBS and NTG-Placebo group. There is no significance between the PBS and NTG-PLACEBO-group.

Figure 8:
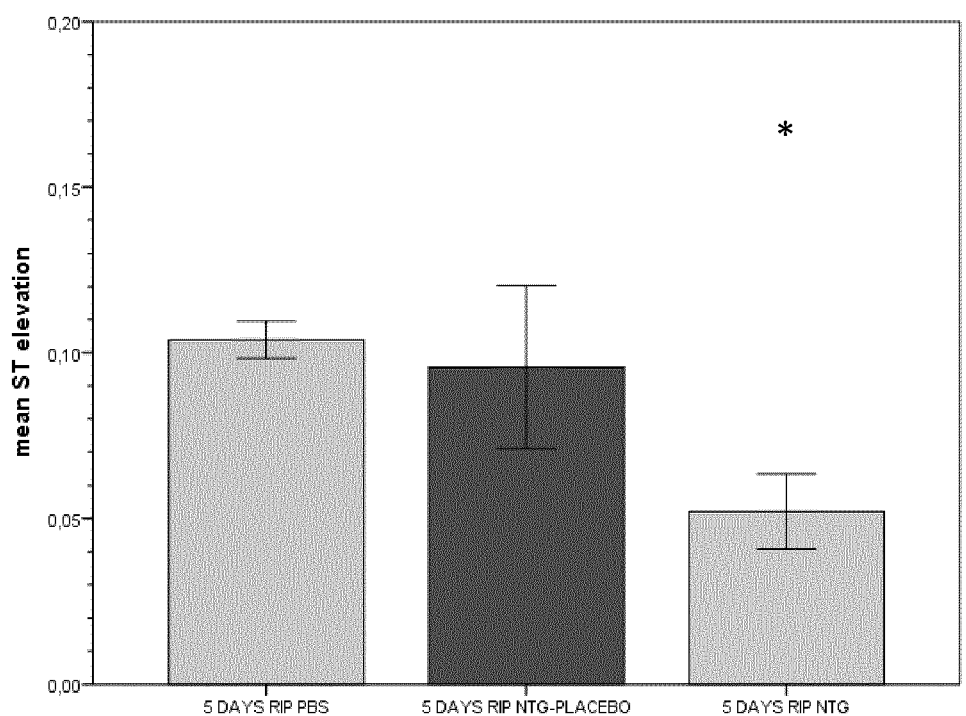

FIG. 8: ST segment elevation (module 2: NO intermittent (NTG)). Column 1 shows 5 DAYS RIP PBS; column 2 shows 5 DAYS NTG-PLACEBO; column 3 shows 5 DAYS RIP NTG; standard deviation is indicated by error bars, asterisk indicates significant decrease of ST segment elevation compared to PBS and NTG-Placebo group (nominal p-value<0.017).

Diagram shows mean of ST segment elevation maximum per group. After treatment with NTG, the ST segment elevation maximum was significantly decreased compared to PBS and NTG-Placebo treatment 5 days after RIP (nominal p-value<0.017).

Figure 9:
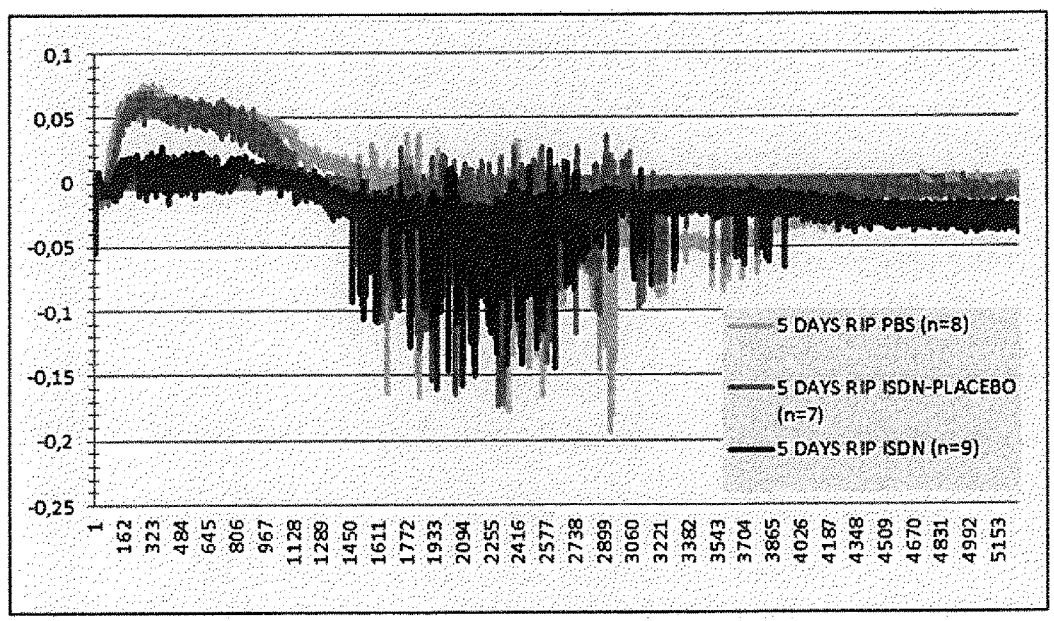

FIG. 9: Course of the ST segment elevation per beat after FPO (module 3: NO continuous (ISDN retard)). ECG graph in light grey indicates 5 DAYS RIP PBS, n=8: 0.104±0.016 mV; ECG graph in middle grey indicates 5 DAYS ISDN-PLACEBO, n=7: 0.110±0.069 mV; ECG graph in black indicates 5 DAYS RIP ISDN, n=7: 0.062±0.027 mV.

Compared to control treatment with PBS or ISDN-Placebo a lower ST segment elevation course was detected after ISDN treatment 5 days after RIP.

ST segment elevation in the ISDN group ("5 DAYS RIP ISDN") is decreased compared to the PBS group but there is no significance as well as between the PBS and ISDN-PLACEBO-group.

Figure 10:
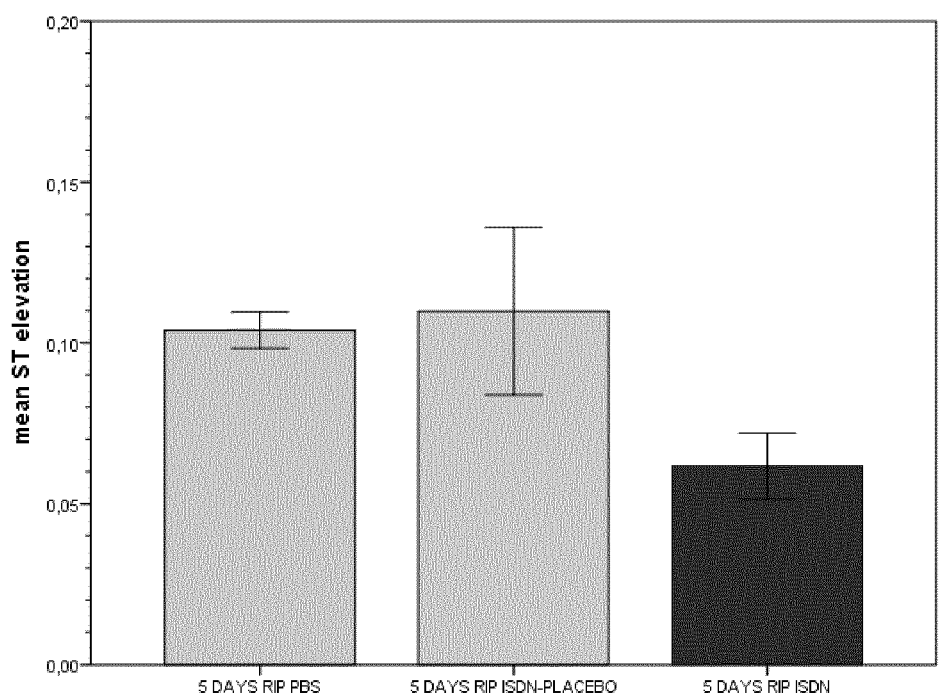

FIG. 10: ST segment elevation (module 3: NO continuous (ISDN retard)). Column 1 shows 5 DAYS RIP PBS; column 2 shows 5 DAYS RIP ISDN-PLACEBO; column 3 shows 5 DAYS RIP ISDN; standard deviation is indicated by error bars.

Diagram shows mean of ST segment elevation maximum per group. After treatment with ISDN, the ST segment elevation maximum was non-significantly decreased compared to PBS and ISDN-Placebo treatment 5 days after RIP.

Figure 11:
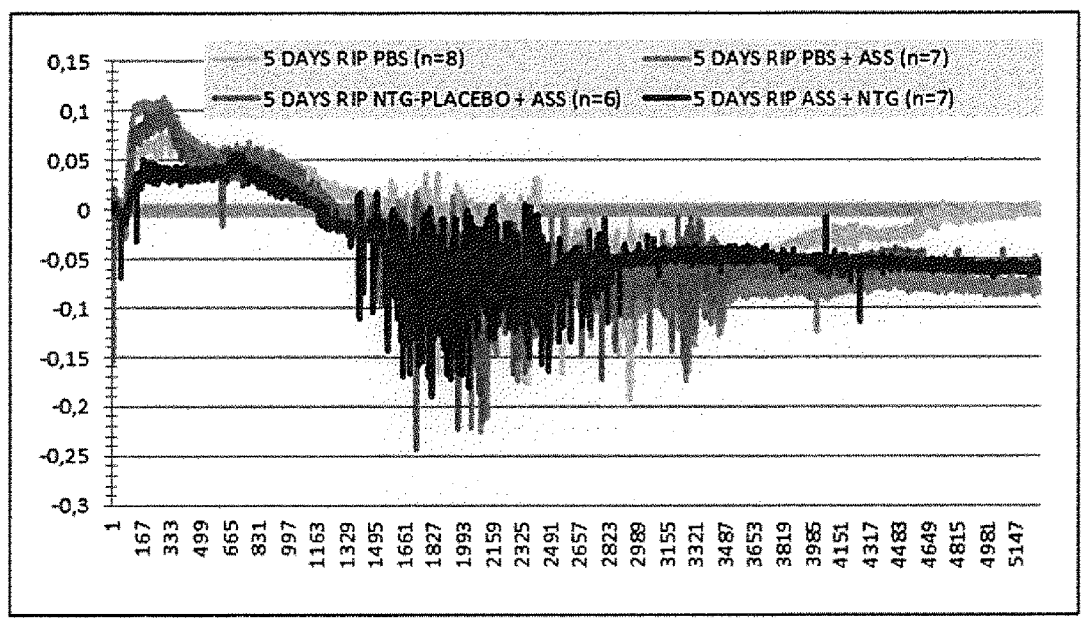

FIG. 11: Course of the ST segment elevation per beat after FPO (module 4: NO intermittent plus ASA). ECG graph in light grey indicates 5 DAYS RIP PBS, n=8; 0.104±0.016 mV; ECG graph in middle grey indicates 5 DAYS RIP ASA+PBS, n=7: 0.138±0.098 mV; ECG graph in dark grey indicates 5 DAYS RIP ASA+NTG-PLACEBO, n=6: 0.144±0.091 mV; ECG graph in black indicates 5 DAYS RIP NTG+ASA, n=7: 0.088±0.071 mV.

Treatment with NTG+ASA was compared to with PBS+ASA, NTG-Placebo+ASA and PBS. In general, all curves overlay at the same range.

ST segment elevation in the group treated with PBS and ASA is higher compared to the PBS control group, but there is no significance as well as between the ASA+NTG-PLACEBO-group. In the ASA+NTG-group ST segment elevation is decreased compared to the group treated with ASA and PBS.

Figure 12:
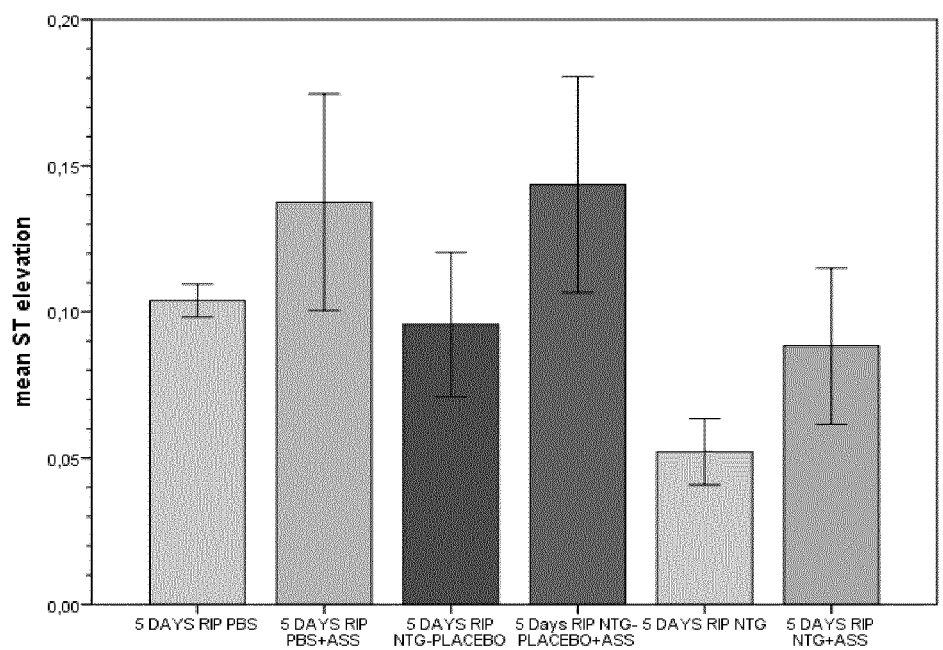

FIG. 12: ST segment elevation (module 4: NO intermittent plus ASA). Column 1 shows 5 DAYS RIP PBS; column 2 shows 5 DAYS RIP PBS+ASA; column 3 shows 5 DAYS RIP NTG-PLACEBO; column 4 shows 5 DAYS RIP NTG-PLACEBO+ASA; column 5 shows 5 DAYS RIP NTG; column 6 shows 5 DAYS RIP NTG+ASA; standard deviation is indicated by error bars.

Diagram shows mean of ST segment elevation maximum per group. Treatment with NTG+ASA was compared to PBS+ASA, NTG-Placebo+ASA and PBS. Furthermore, all ASA groups (PBS+ASA, NTG-Placebo+ASA, NTG+ASA) were compared to their controls (PBS, NTG-Placebo, NTG). No significant differences were detected.

Figure 13:
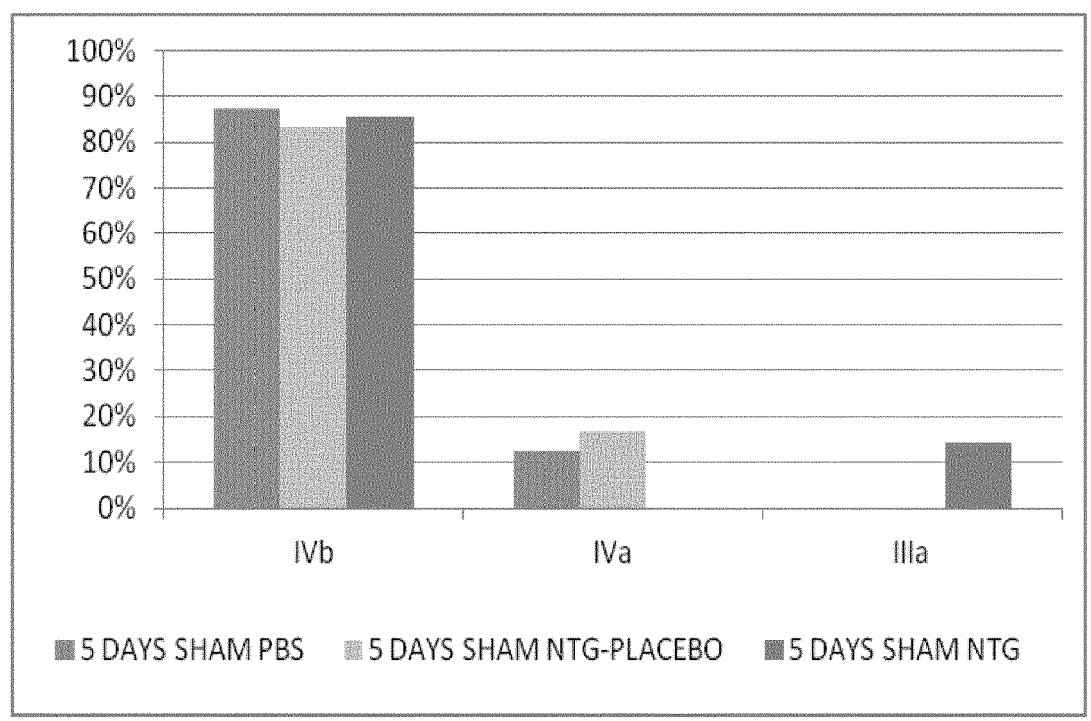

FIG. 13: Arrhythmias during FPO (module 1: Sham Operation (without the RIP)). Numbers of columns are given in consecutive order of the columns in group IVb. Column 1 shows 5 DAYS SHAM PBS; column 2 shows 5 DAYS SHAM NTG-PLACEBO; column 3 shows 5 DAYS SHAM NTG.

In accordance with Lown classification, all sham groups were predominantly scaled into grade IVb.

In the "5 DAYS SHAM PBS" group 87.5% of the rats have class IVb arrhythmias and 12.5% class IVa. In the "5 DAYS SHAM NTG-PLACEBO" group 83.3% have IVb arrhythmias and 16.7% class IVa and in the "5 DAYS SHAM NTG" group 85.7% have IVb arrhythmias and 14.3% class IIIa arrhythmias.

Figure 14:
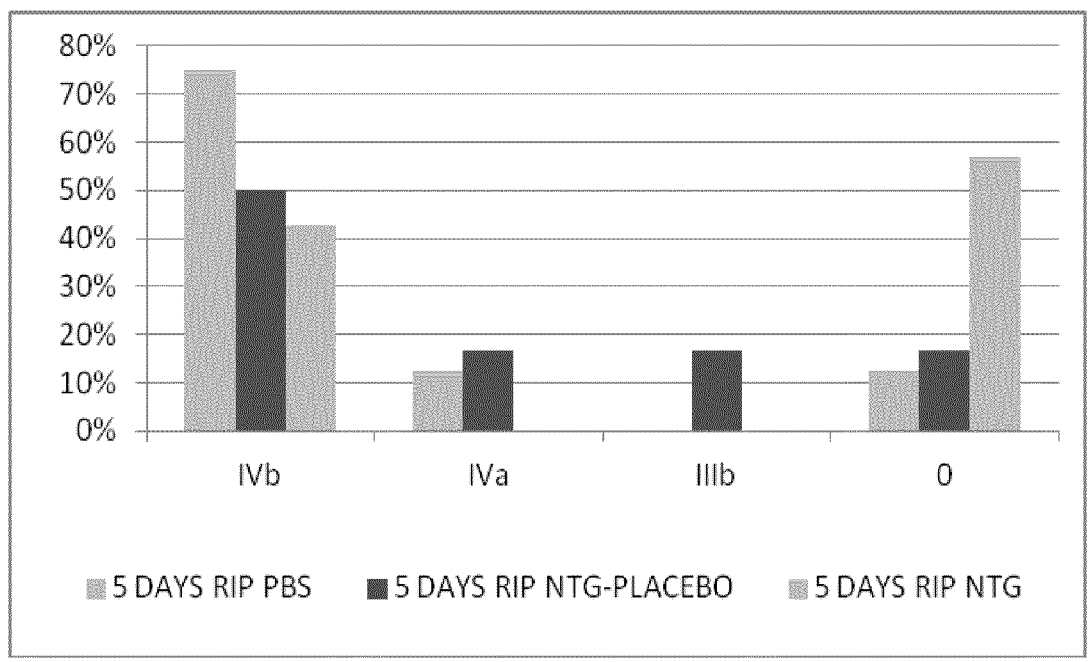

FIG. 14: Arrhythmias during FPO (module 2: NO intermittent (NTG)). Numbers of columns are given in consecutive order of the columns in group IVb. Column 1 shows 5 DAYS RIP PBS; column 2 shows 5 DAYS RIP NTG-PLACEBO; column 3 shows 5 DAYS RIP NTG.

While arrhythmias in both control groups, PBS and NTG-Placebo, were predominantly scaled into grade IVb, the NTG treated group was more often scaled into grade 0.

In the "5 DAYS RIP PBS" group, 75.0% of the rats have class IVb arrhythmias, 12.5% IVa and 12.5% class 0. Regarding the "5 DAYS RIP NTG-PLACEBO" group, 50.0% of the rats showed class IVb arrhythmias, 16.7% IVa, 16.7% class IIIb and 16.7% class 0 arrhythmias. Interestingly, the "5 DAYS RIP NTG" group shows 42.9% class IVb arrhythmias and 57.1% class 0 arrhythmias.

Figure 15:
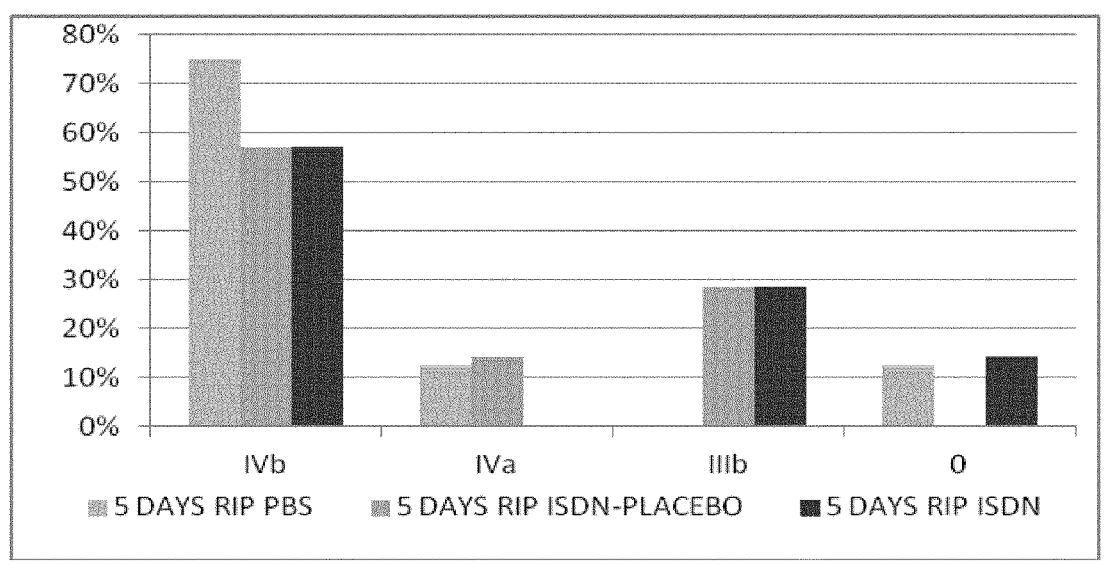

FIG. 15: Arrhythmias during FPO (module 3: NO continuous (ISDN retard)). Numbers of columns are given in consecutive order of the columns in group IVb. Column 1 shows 5 DAYS RIP PBS; column 2 shows 5 DAYS RIP ISDN-PLACEBO; column 3 shows 5 DAYS RIP ISDN.

In all groups, arrhythmias were similarly more often scaled into grade IVb.

In the "5 DAYS ISDN-PLACEBO" group, 57.1% of the rats have class IVb arrhythmias, 14.3% class IVa and 28.6% class IIIb. The "5 DAYS RIP ISDN" group shows less severe arrhythmias with 57.1% class IVb, 28.6% class IIIb and 14.3% class 0 arrhythmias.

Figure 16:
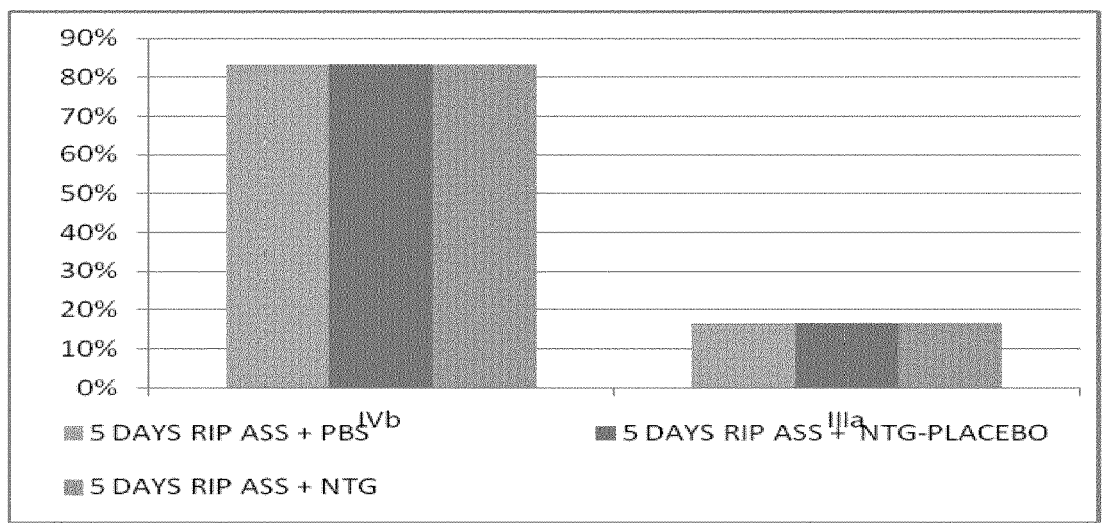

FIG. 16: Arrhythmias during FPO (module 4: NO intermittent plus ASA). Numbers of columns are given in consecutive order of the columns in group IVb. Column 1 shows 5 DAYS RIP ASA+PBS; column 2 shows 5 DAYS RIP ASA+NTG-PLACEBO; column 3 shows 5 DAYS RIP ASA+NTG.

Arrhythmias were similarly scaled more into grade IVb in all groups.

In the "5 DAYS RIP ASA+PBS" group, in the group treated with ASA+NTG-PLACEBO and in the "5 DAYS RIP ASA+NTG" group 83.3% of the rats posses class IVb arrhythmias and 16.7% class IIIc.

Figure 17:
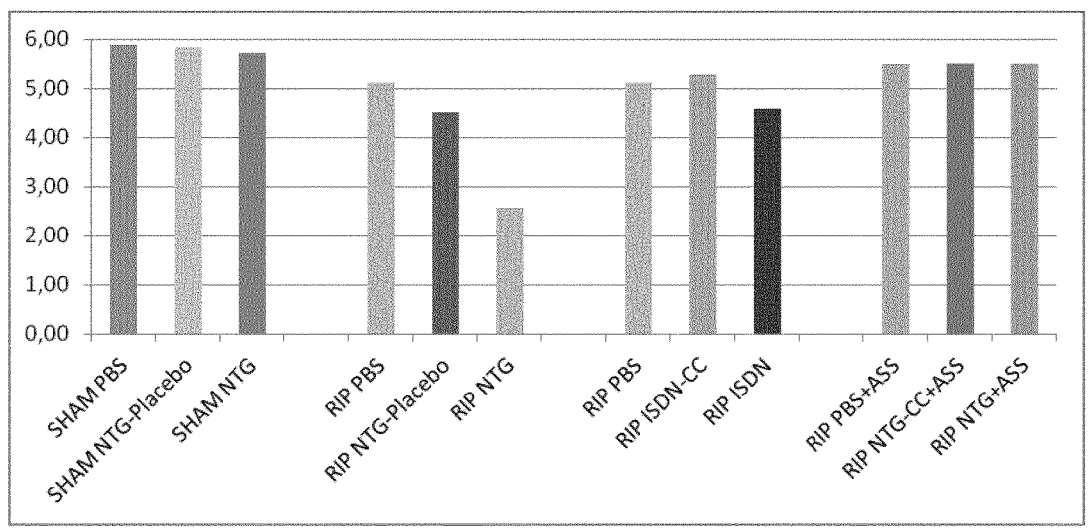

FIG. 17: VPB-Score. Column 1 shows SHAM PBS; column 2 shows SHAM NTG-Placebo; column 3 shows SHAM NTG; column 4 shows RIP PBS; column 5 shows RIP NTG-Placebo; column 6 shows RIP NTG; column 7 shows RIP PBS; column 8 shows RIP ISDN-Placebo column 9 shows RIP ISDN; column 10 shows RIP PBS+ASA; column 11 shows RIP NTG-Placebo+ASA; column 12 shows RIP NTG+ASA.

Regarding the percentage of each Lown grade of every group, a VBP score can be ascertained. The more animals show a higher grade, the higher is the VBP score.

The VBP score shows the percentage of each Lown grade of every group. The Sham-groups have higher VBP-scores. Compared to the group with an ischemic protocol (control group, treated with PBS), more rats show severe arrhythmias. The treatment with NTG revealed reduced arrhythmias, and consequently a lower VPB-Score. The VPB-Score in groups treated with ASA alone or NTG+ASA is higher compared to the controls (treated with PBS).

Figure 18:
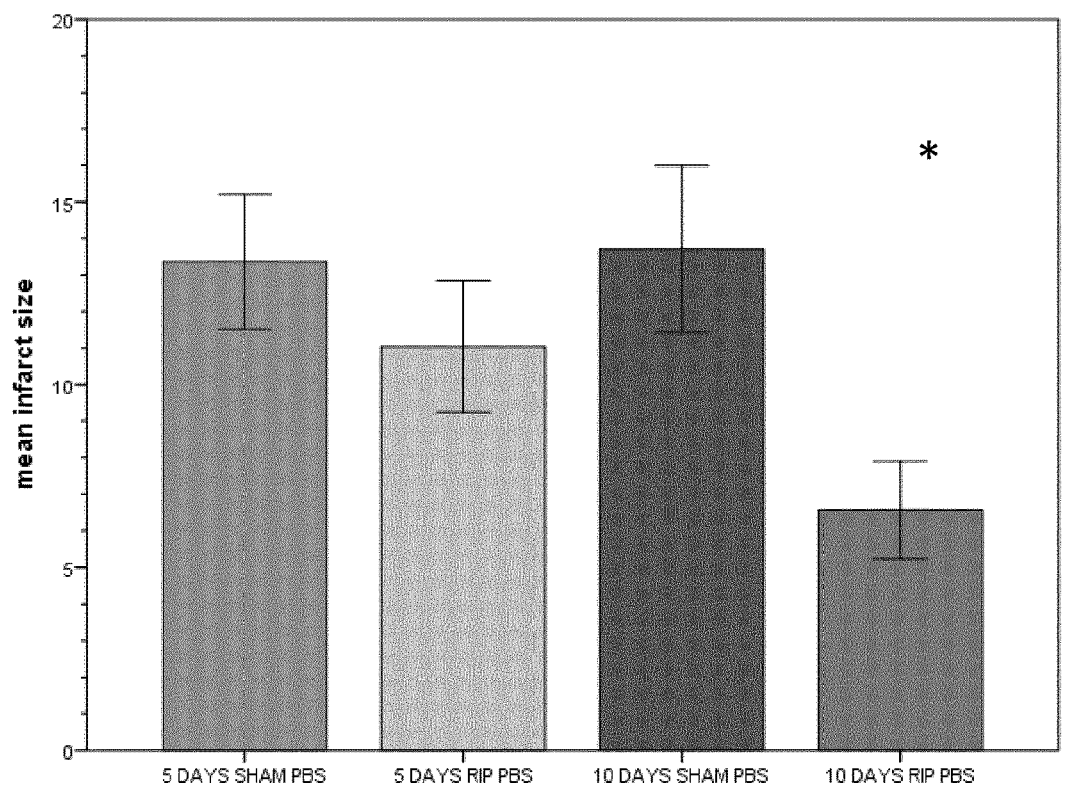

FIG. 18: Infarct size of 5-days- and 10-days-control-groups. Column 1 shows 5 DAYS SHAM PBS, n=8: 13.36±5.22%; column 2 shows 5 DAYS RIP PBS, n=8: 11.05±5.12%; column 3 shows 10 DAYS SHAM PBS, n=7: 13.71±6.04%; column 4 shows 10 DAYS RIP PBS, n=6: 6.57±3.26%; standard deviation is indicated by error bars; asterisk indicates significant compared to the shams (nominal p-value<0.013).

After an ischemic protocol of 5 days there is no significantly smaller infarct size measurable, but after a RIP of 10 days the infracted area is significantly decreased compared to the shams (nominal p-value<0.013).

After 90 minutes of LAD occlusion and 20 minutes reperfusion, infarct size was analyzed.

The "10 DAYS RIP PBS" group has a significantly smaller infarct area compared to the "10 DAYS SHAM PBS" group. There is no significance between both 5 DAYS groups.

Figure 19:
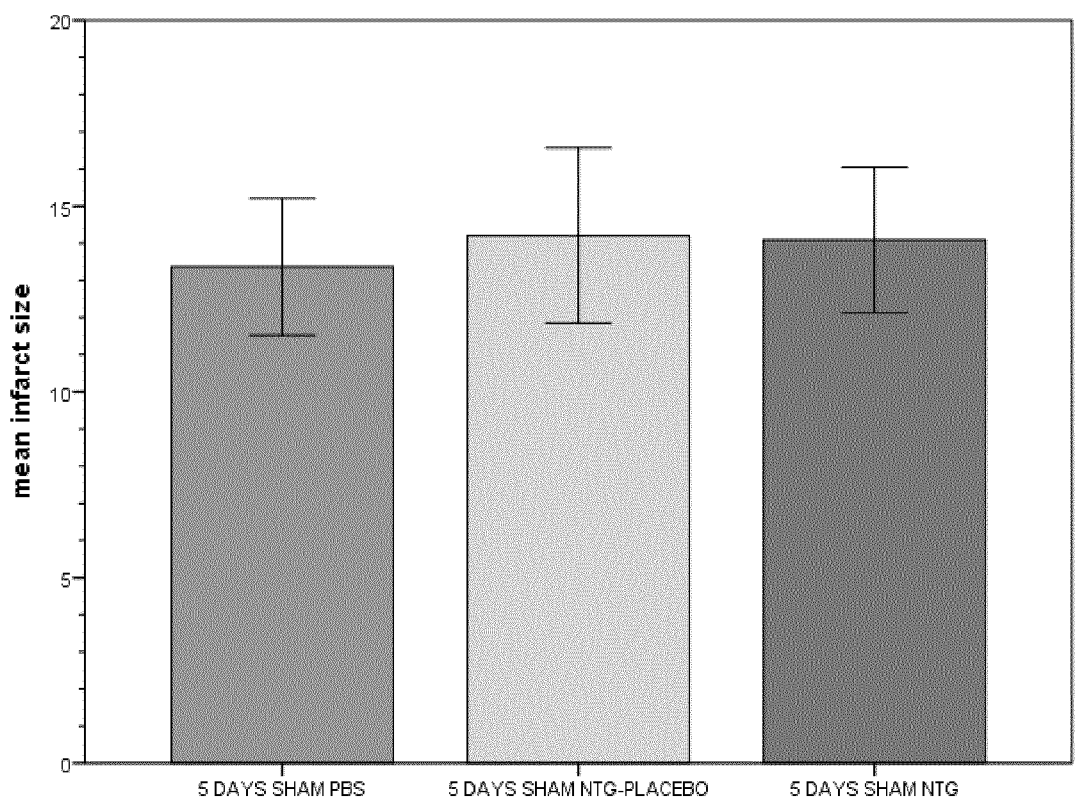

FIG. 19: Infarct size (module 1: Sham Operation (without the RIP)). Column 1 shows 5 DAYS SHAM PBS, n=8: 13.36±5.22%; column 2 shows 5 DAYS SHAM NTG-PLACEBO, n=6: 14.21±5.79%; column 3 shows 5 DAYS SHAM NTG, n=7: 14.09±5.18%; standard deviation is indicated by error bars.

The infarct size shows no difference between the SHAM groups.

There is no significance between the three SHAM groups.

Figure 20:
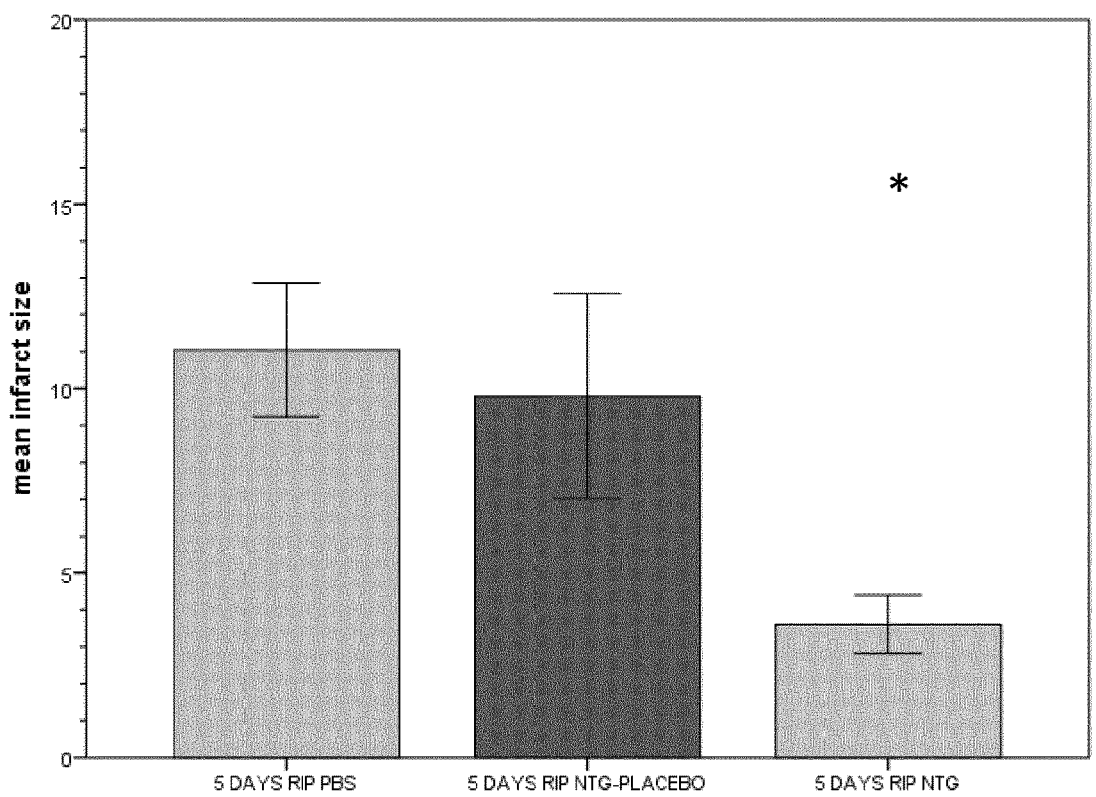

FIG. 20: Infarct size (module 2: NO intermittent (NTG)). Column 1 shows 5 DAYS RIP PBS, n=8: 11.05±5.12%; column 2 shows 5 DAYS NTG-PLACEBO: n=6; 9.80±6.79%; column 3 shows 5 DAYS RIP NTG, n=7: 3.61±2.08%; standard deviation is indicated by error bars, asterisk indicates significant compared to 5 DAYS RIP PBS (nominal p-value<0.017).

The infarct size is significantly smaller after treatment with NTG compared to controls (treated with PBS) (nominal p-value<0.033).

Compared to the "5 DAYS RIP PBS", a significantly smaller infarct area is observed in the "5 DAYS RIP NTG" group. There is no significance between the PBS and NTG-PLACEBO-group.

Figure 21:
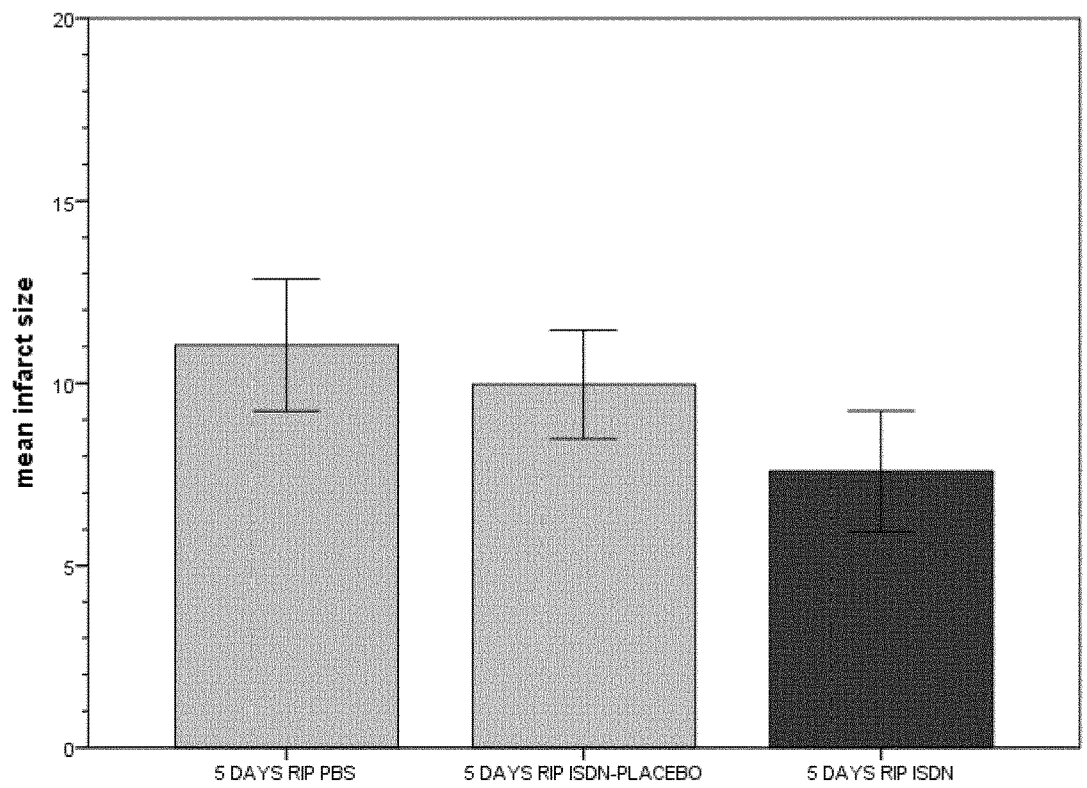

FIG. 21: Infarct size (module 3: NO continuous (ISDN retard)). Column 1 shows 5 DAYS RIP PBS, n=8: 11.05±5.12%; column 2 shows 5 DAYS ISDN-PLACEBO, n=6: 9.97±3.65%; column 3 shows 5 DAYS RIP ISDN, n=7: 7.59±4.38%; standard deviation is indicated by error bars.

The infarct size after treatment with ISDN is smaller compared to controls (treated with PBS or ISDN-Placebo), but there is no significance.

The infarct size in the ISDN group ("5 DAYS RIP ISDN") is smaller compared to the PBS group, as well as the ISDN-PLACEBO-group.

Figure 22:
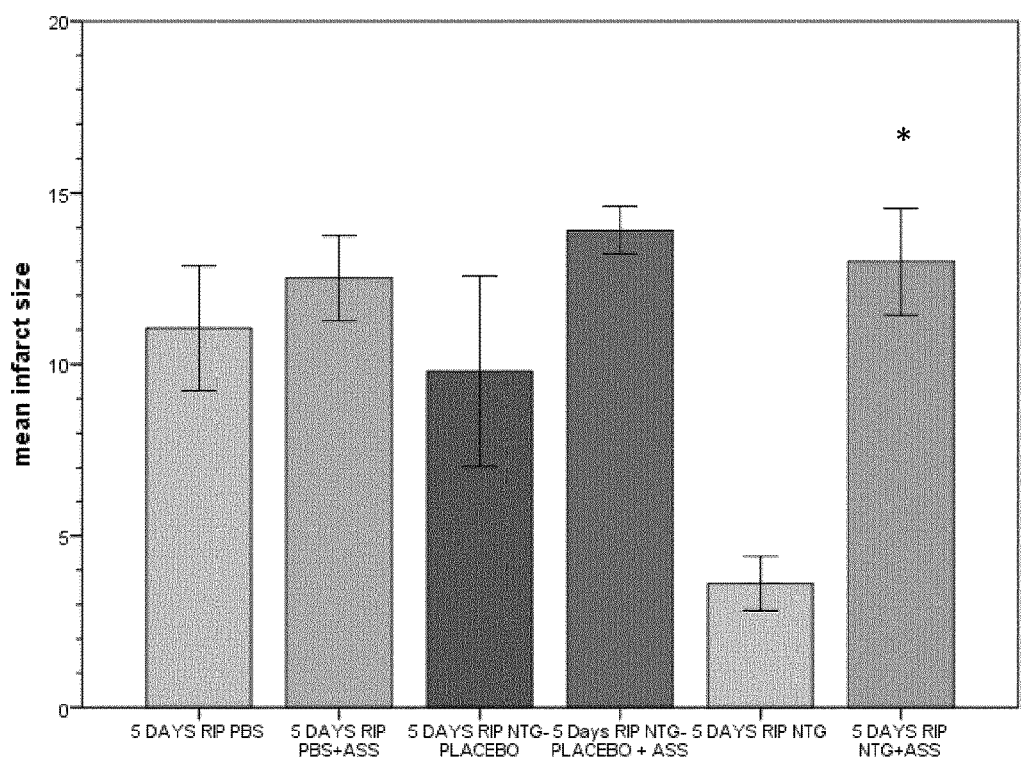

FIG. 22: Infarct size (module 4: NO intermittent plus ASA). Column 1 shows 5 DAYS RIP PBS, n=8: 11.05±5.12%; column 2 shows 5 DAYS RIP ASA+PBS, n=6: 12.51±3.05%; column 3 shows 5 DAYS NTG-PLACEBO: n=6; 9.80±6.79%; column 4 shows 5 DAYS RIP NTG-PLACEBO+ASA, n=6: 13.92±1.71%; column 5 shows 5 DAYS RIP NTG, n=7: 3.61±2.08%; column 6 shows 5 DAYS RIP NTG+ASA, n=6: 13.00±3.82%; standard deviation is indicated by error bars, asterisk indicates significant compared to 5 DAYS RIP NTG (nominal p-value<0.017).

The infarct size after treatment with NTG plus ASA is significantly increased compared to the treatment with NTG alone (nominal p-value<0.017).

The infarct size in the group treated with ASA ("5 DAYS ASA+PBS") is minimally increased compared to the PBS control group, as well as the ASA+NTG-PLACEBO-group. There is no difference between the ASA+NTG-group and the group treated with ASS and PBS. However, the infarct area in the NTG group is significantly smaller compared to the ASA+NTG group.

Figure 23:
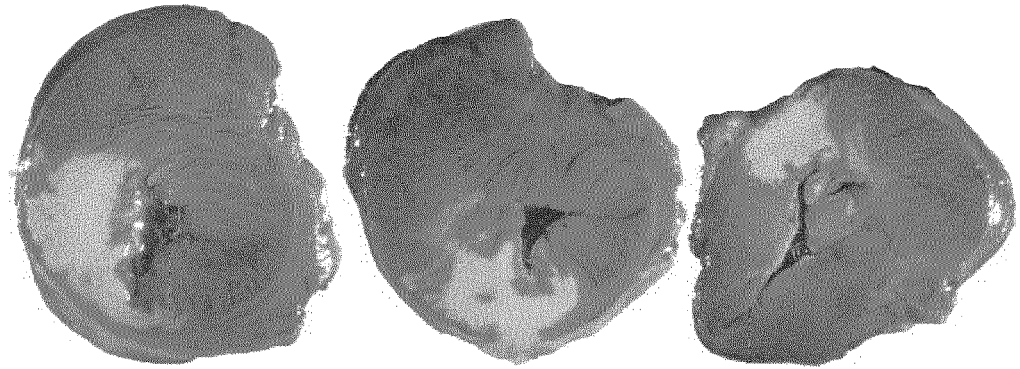
Figure 23:
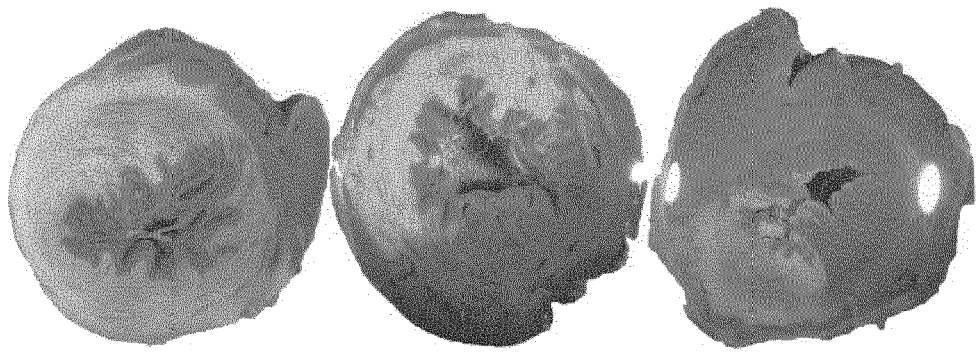
Figure 23:
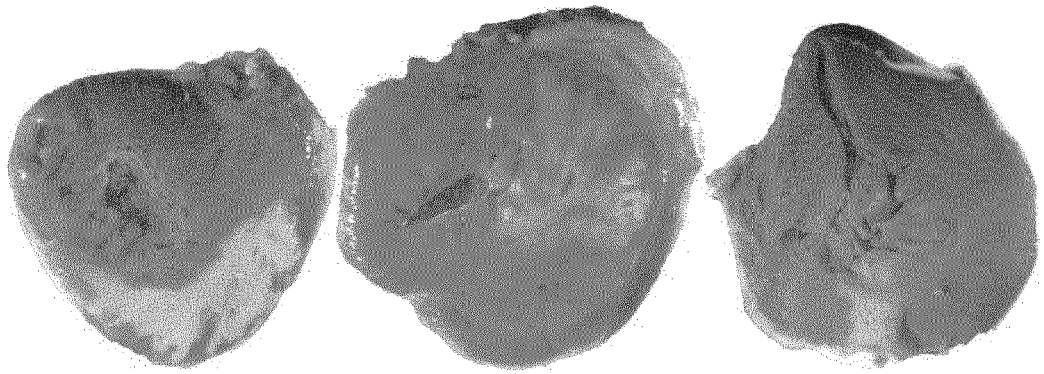
Figure 23:
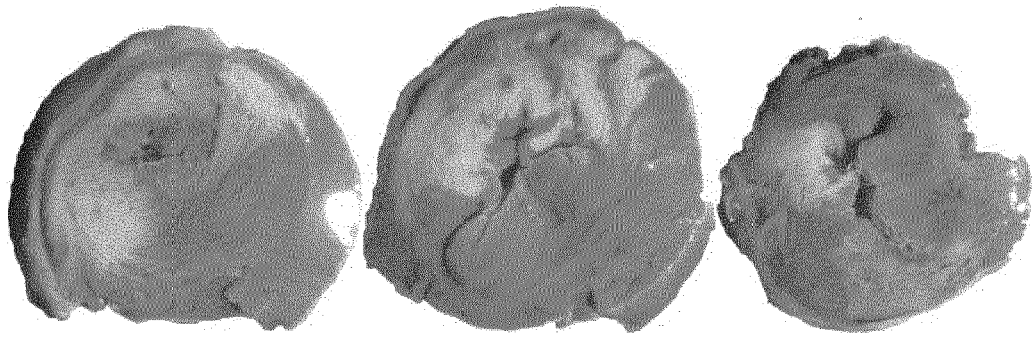
Figure 23:
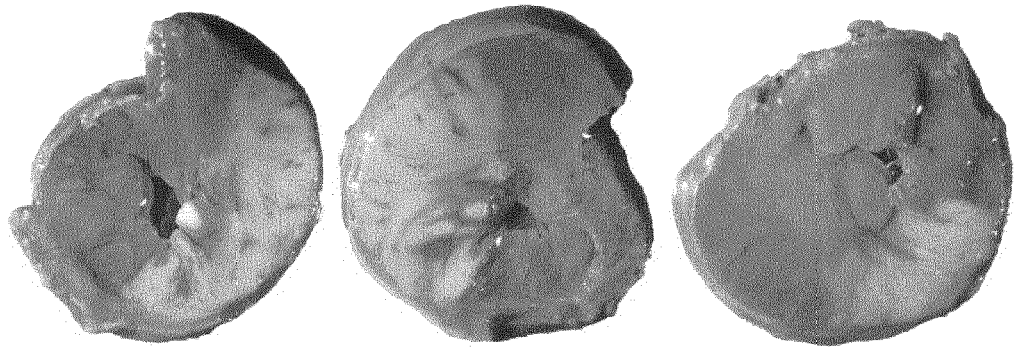
Figure 23:
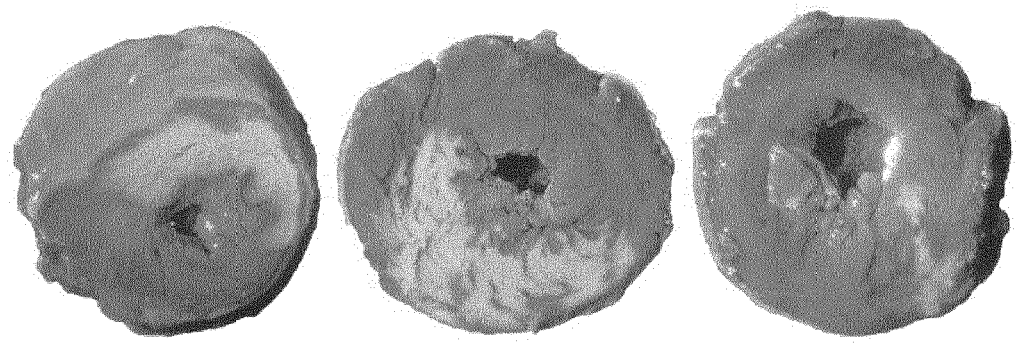
Figure 23:
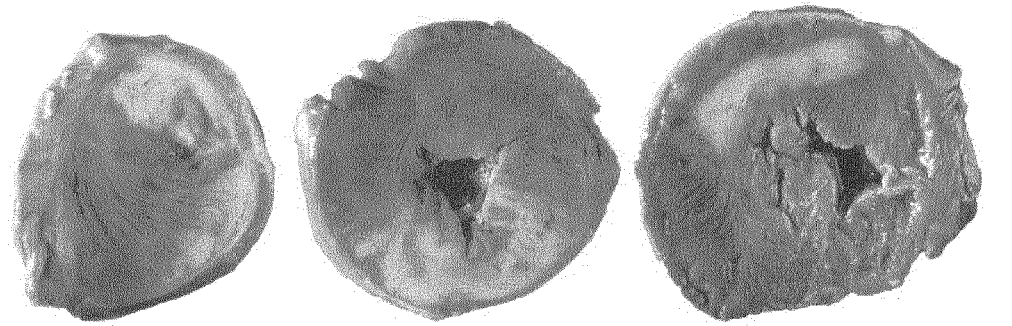
Figure 23:
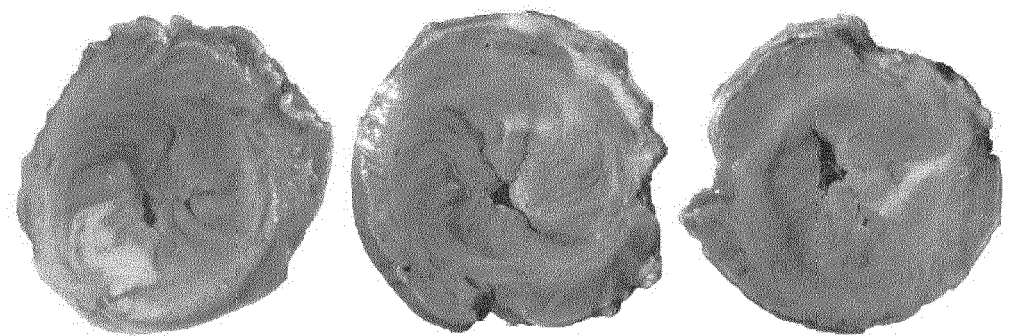
Figure 23:
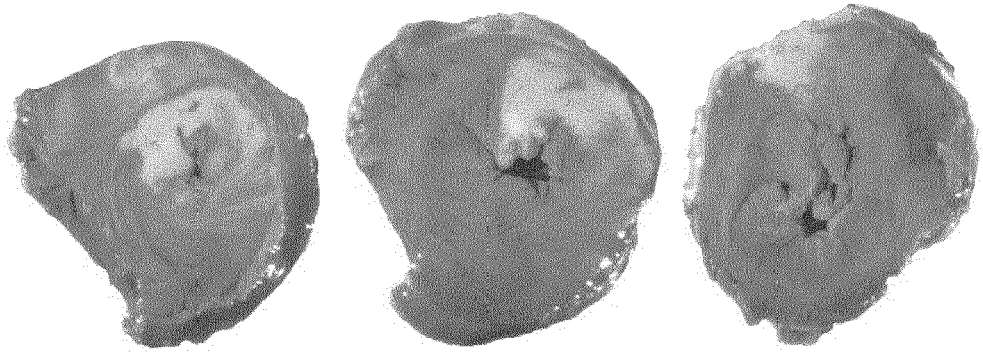
Figure 23:
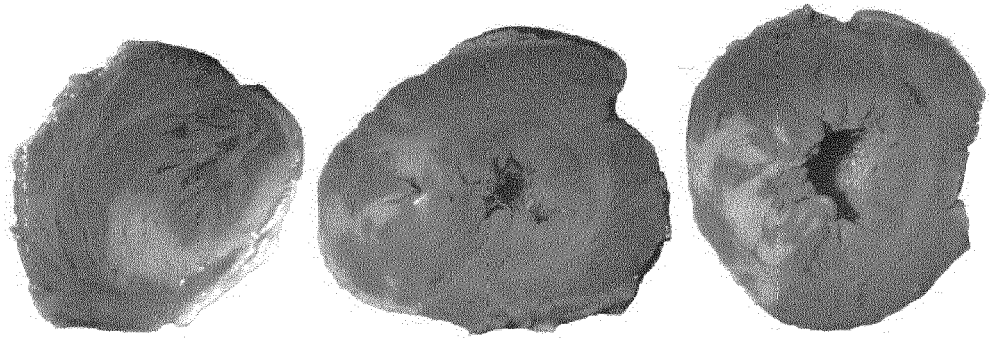
Figure 23:
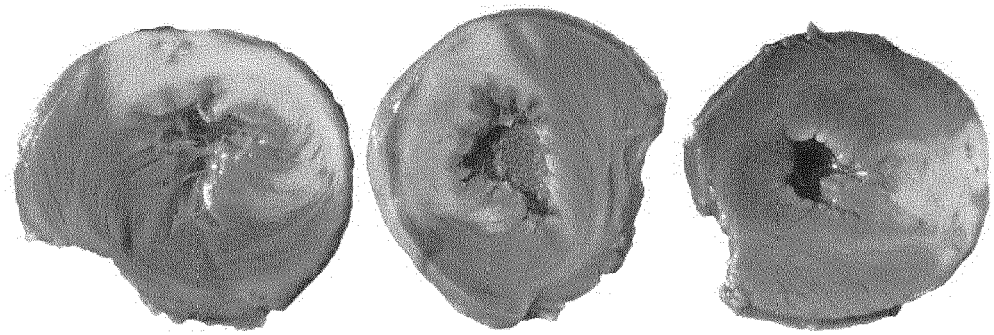
Figure 23:
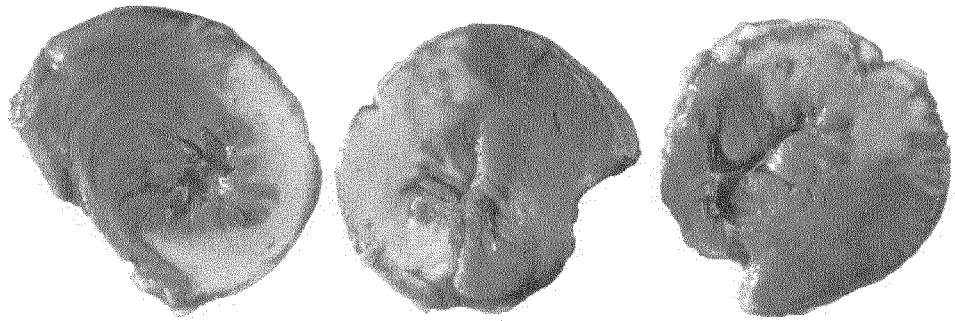
Figure 23:
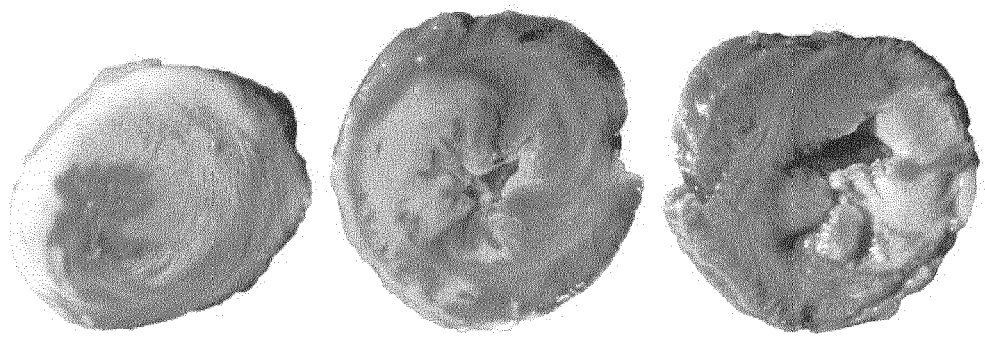

FIG. 23: TTC-staining. The pictures show slices of three levels. Infarcted tissue stains a pale-white since they lack the enzymes with which the TTC reacts. Thus the areas of necrosis are clearly discernible and quantifiable.

Figure 24:
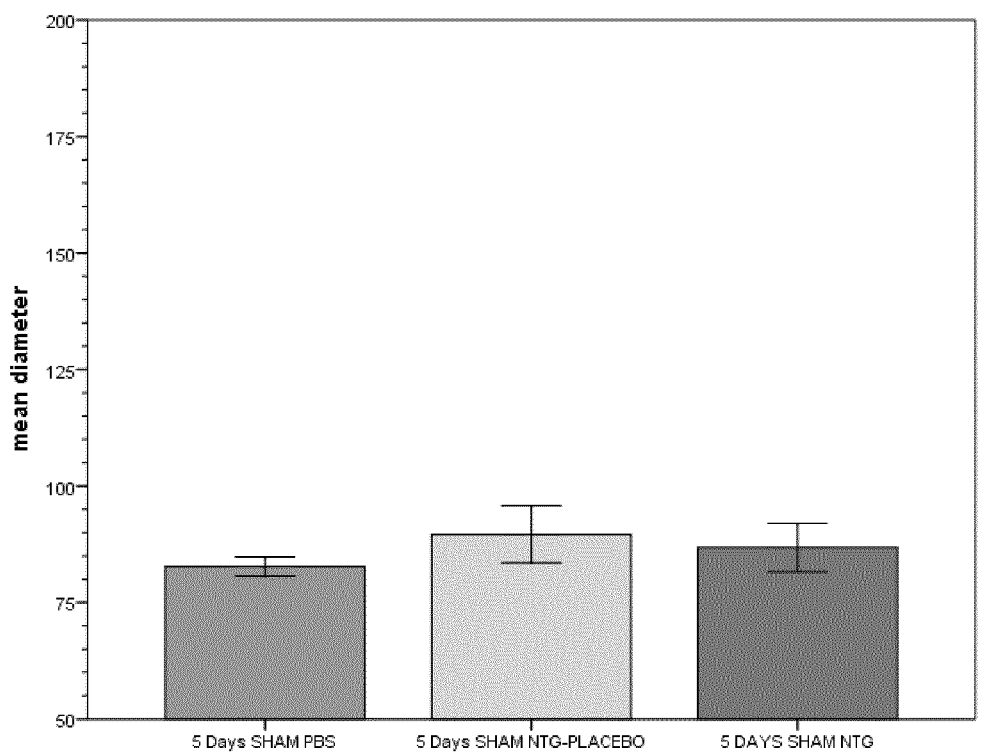

FIG. 24: Collateral diameters of ROI (module 1: Sham Operation (without the RIP)). Column 1 shows 5 DAYS SHAM PBS, n=3: 82.7±3.7 µm; column 2 shows 5 DAYS SHAM NTG-PLACEBO, n=3: 89.6 µm±10.6 µm; column 3 shows 5 DAYS SHAM NTG, n=3: 86.8±9.0 µm; standard deviation is indicated by error bars.

There is no growth of collaterals and no differences measurable between the SHAM groups.

There is no significance between the three SHAM-groups.

Figure 25:
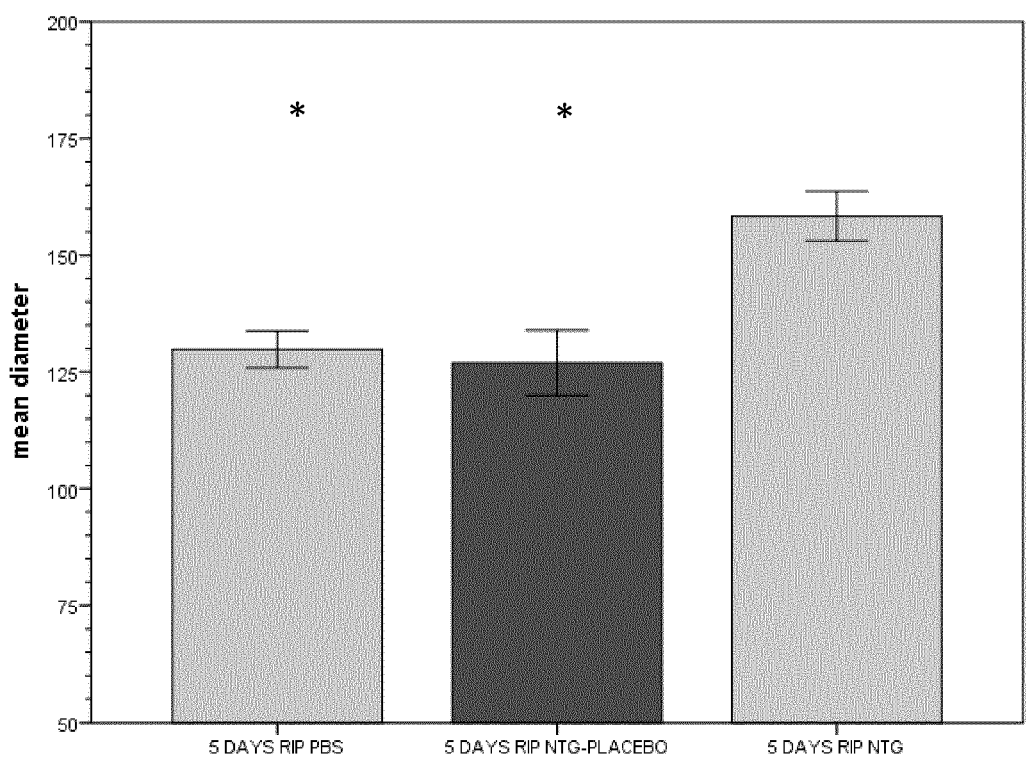

FIG. 25: Collateral diameters of ROI (module 2: NO intermittent (NTG)). Column 1 shows 5 DAYS RIP PBS, n=3: 129.8±6.9 µm; column 2 shows 5 DAYS RIP NTG-PLACEBO: n=3; 127.0±12.1 µm; column 3 shows 5 DAYS RIP NTG, n=3: 158.4±9.2 µm; standard deviation is indicated by error bars, asterisk indicates significant compared to 5 DAYS RIP NTG (nominal p-value<0.033). Diameters of collaterals are significantly increased by treatment with NTG compared to controls (treated with PBS or NTG-Placebo) (nominal p-value<0.033).

Compared to the "5 DAYS RIP PBS", the diameters of the collaterals in the ROI in the "5 DAYS RIP NTG" group are significantly increased. There is no difference between the PBS and NTG-PLACEBO-group.

Figure 26:
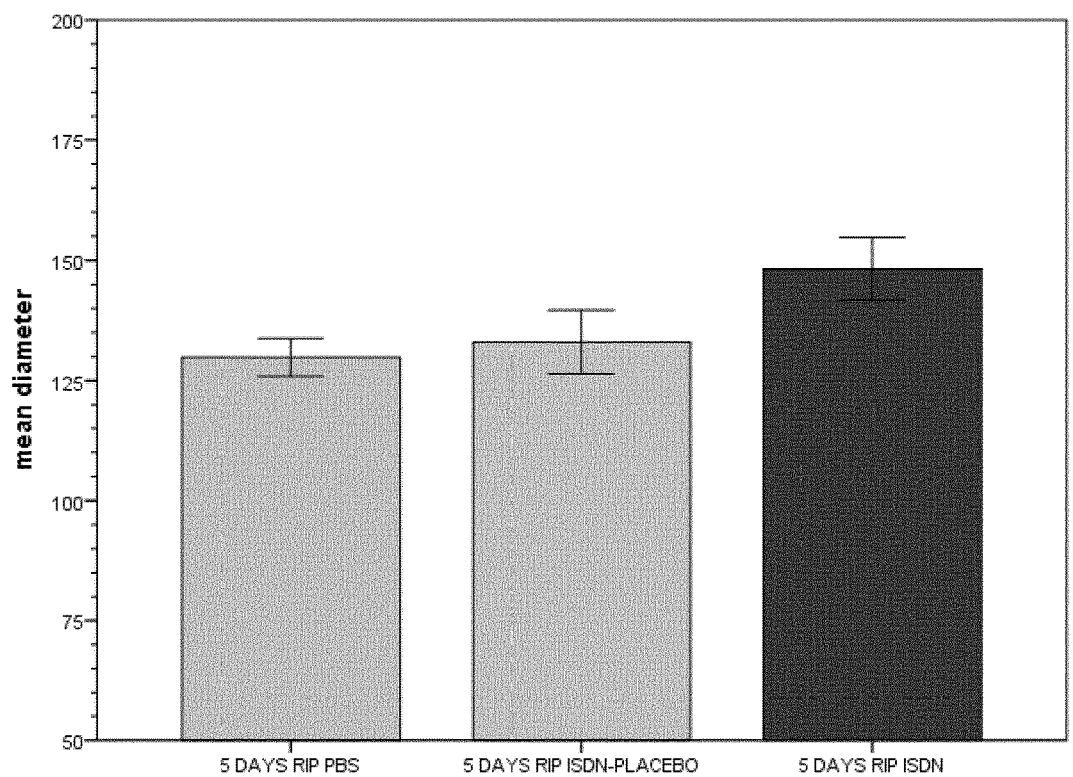

FIG. 26: Collateral diameters of ROI (module 3: NO continuous (ISDN retard)). Column 1 shows 5 DAYS RIP PBS, n=3: 129.8±6.9 µm; column 2 shows 5 DAYS ISDN-PLACEBO, n=3: 133.0±11.5 µm; column 3 shows 5 DAYS RIP ISDN, n=3: 148.2±11.3 µm; standard deviation is indicated by error bars.

No differences are measurable in the diameter of collaterals after treatment with ISDN or ISDN-Placebo.

The diameters of the collaterals in the ISDN group ("5 DAYS RIP ISDN") are enhanced compared to the PBS group, as well as compared to the ISDN-PLACEBO group.

Figure 27:
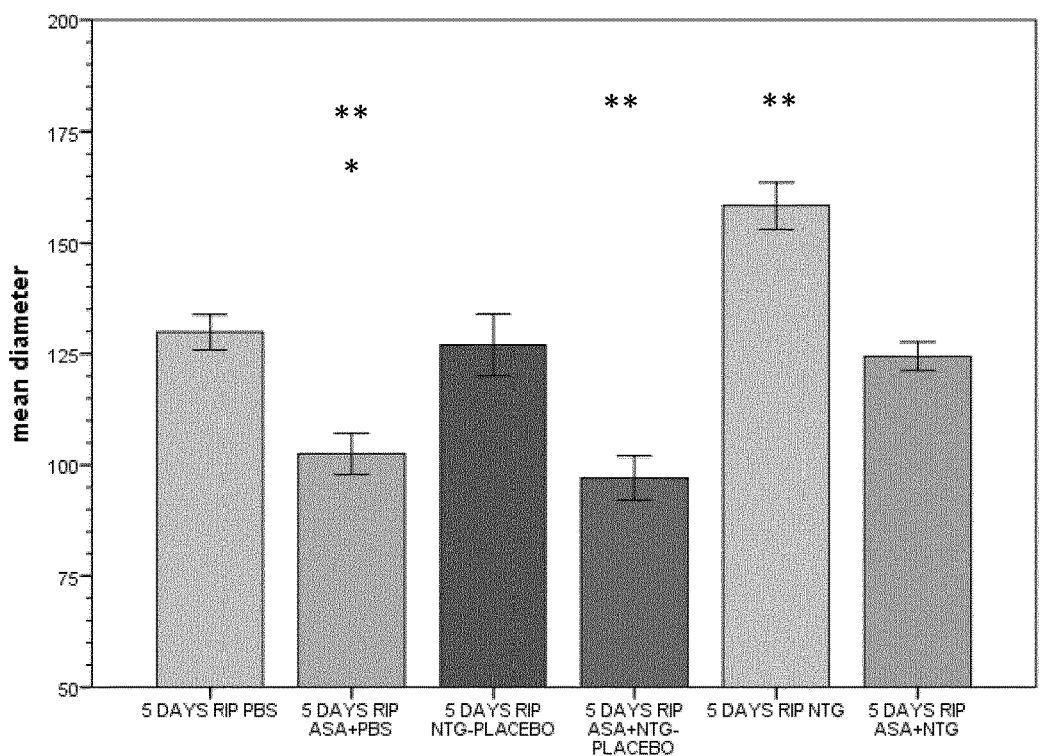

FIG. 27: Collateral diameter of ROI (module 4: NO intermittent plus ASA). Column 1 shows 5 DAYS RIP PBS, n=3; 129.8±6.9 µm; column 2 shows 5 DAYS RIP PBS+ASA, n=3: 102.5±8.0 µm; column 3 shows 5 DAYS RIP NTG-PLACEBO: n=3; 127.0±12.1 µm; column 4 shows 5 DAYS NTG-PLACEBO+ASA, n=3: 97.1±8.6 µm; column 5 shows 5 DAYS RIP NTG, n=3: 158.4±9.2 µm; column 6 shows 5 DAYS RIP ASA+NTG, n=3: 124.4±5.6 µm; standard deviation is indicated by error bars, one asterisk indicates significant compared to 5 DAYS RIP PBS (nominal p-value<0.039); double asterisk indicates significant compared to 5 DAYS RIP ASA+NTG (nominal p-value<0.039).

Diameters of collaterals are significantly smaller after treatment with ASA compared to control (treated with PBS) (nominal p-value<0.039). An additional treatment with NTG abolished the inhibiting effect of ASA, but NTG-treatment alone shows significantly increased diameter compared to treatment with NTG+ASA (**significant compared to 5 DAYS RIP ASA+NTG, nominal p-value<0.039).

The diameters in the group treated with PBS and ASA are significantly smaller compared to the PBS control group, but there is no significance compared to the ASA+NTG-PLA-CEBO-group. In the ASA+NTG-group diameters are significantly increased compared to the group treated with PBS and ASA.

Figure 28:
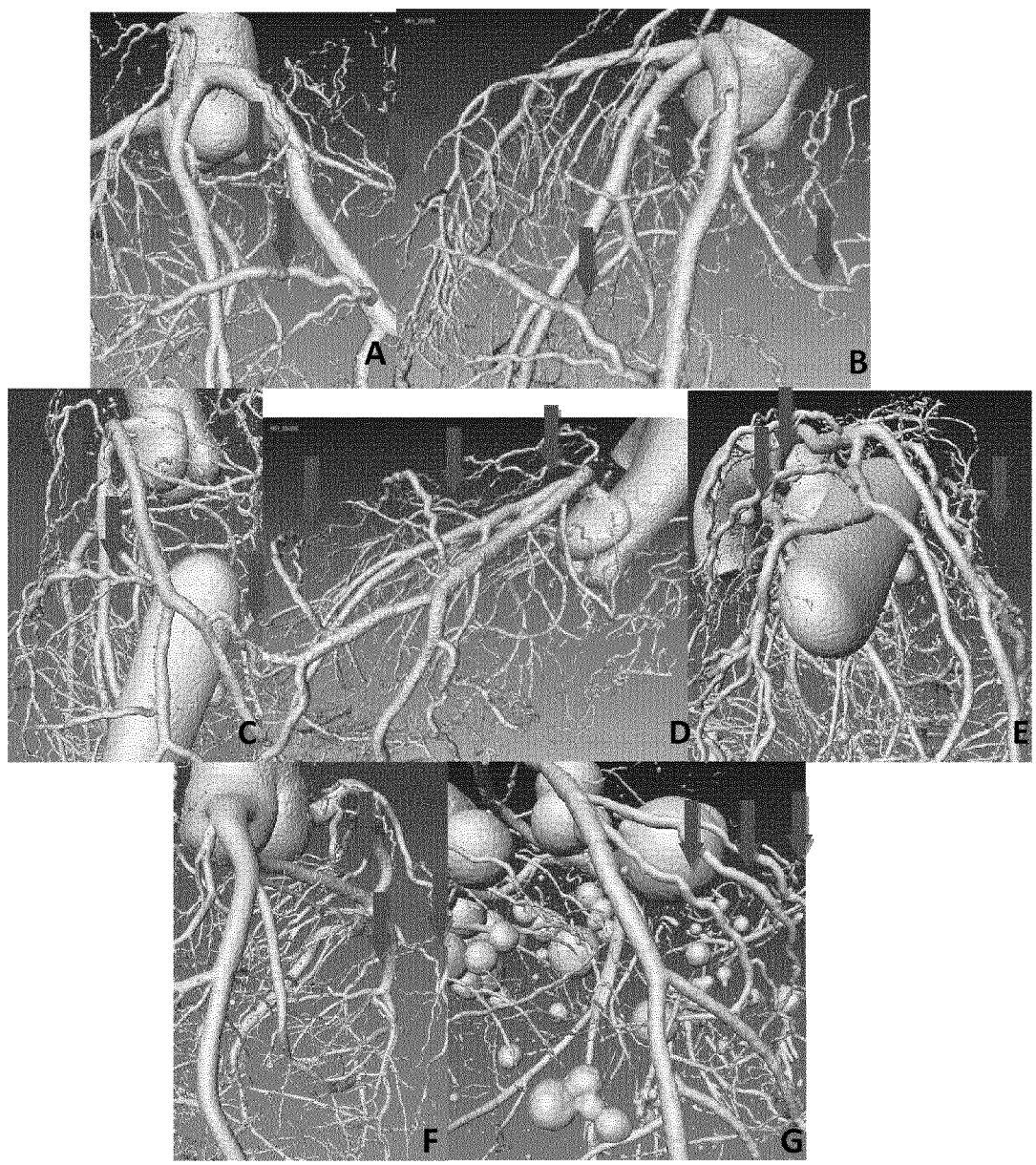

FIG. 28: MicroCT imaging of the "ROI": (A) "5 DAYS SHAM PBS"; (B) "5 DAYS SHAM NTG"; (C) "5 DAYS RIP ISDN"; (D) "5 DAYS RIP PBS"; (E) "5 DAYS RIP NTG"; (F) "5 DAYS RIP ASA+PBS; (G) "5 DAYS RIP ASA+NTG".

The pictures show the growth of the collateral diameter in the region of interest by the ischemic protocol treated with PBS (D), NTG (E), or ISDN (C) compared to SHAM treated with PBS (A) or NTG (B). Inhibition of collateral growth by treatment with ASA (F) is partially abolished by additional treatment with NTG (G).

EXAMPLES

Example 1

450.2 g xylitol and 45.0 g tyloxapol are dissolved in 937.6 g of purified water. 67.8 g of a 5% solution of GTN in propylene glycol are added and the mixture is stirred intensively for 15 minutes. A clear solution is formed that is stable both at room temperature and at 4° C. The viscosity of this solution is 10 mPa*s.

It is concluded that a 0.225% solution of GTN can be prepared using this formula.

Example 2

45.0 g xylitol and 3.0 g poloxamer 407 are dissolved in 46.0 g of purified water. 5.99 g of a 5% solution of GTN in propylene glycol are added and the mixture is stirred intensively for 15 minutes. A clear solution is formed that is stable both at room temperature and at 4° C. The viscosity of this solution is 17 mPa*s.

It is concluded that a 0.30% solution of GTN can be prepared using this formula.

Example 3

35.5 g xylitol and 1.0 g poloxamer 407 are dissolved in 44.0 g of purified water. 5.01 g of a 5% solution of GTN in propylene glycol are dissolved in 15.0 g ethanol. Both solutions are mixed and the mixture is stirred intensively for 15 minutes. A clear solution is formed that is stable both at room temperature and at 4° C. The viscosity of this solution is 12 mPa*s.

It is concluded that a 0.25% solution of GTN can be prepared using this formula.

Example 4

35.1 g xylitol and 1.0 g tyloxapol are dissolved in 44.0 g of purified water. 5.06 g of a 5% solution of GTN in propylene glycol are dissolved in 15.0 g ethanol. Both solutions are mixed and the mixture is stirred intensively for 15 minutes. A clear solution is formed that is stable both at room temperature and at 4° C. The viscosity of this solution is 10 mPa*s.

It is concluded that a 0.25% solution of GTN can be prepared using this formula.

Example 5

1125.0 g xylitol and 125.1 g poloxamer 407 are dissolved in 1100 g of purified water. 150.0 g of a 5% solution of GTN in propylene glycol are added and the mixture is stirred intensively for 15 minutes. The pH value of the solution is adjusted to pH 4.5 with lactic acid. A clear solution is formed that is stable both at room temperature and at 4° C. Furthermore this solution can be frozen at −20° C. and results in a clear solution after thawing. The viscosity of this solution is 25 mPa*s.

It is concluded that a 0.30% solution of GTN can be prepared using this formula. The long term stability of this solution is excellent as can be seen from the following table:

| Stability at 40° C. | Start | 3 months | 6 months |
| --- | --- | --- | --- |
| GTN assay (HPLC) | 0.296% | 0.293% | 0.287% |
| Stability at 25° C. | Start | 6 months | 12 months |
| GTN assay (HPLC) | 0.296% | 0.293% | 0.294% |

Example 9

30.0 g poloxamer 407 are dissolved in 1169 g of purified water. 75.8 g of a 5 solution of GTN in propylene glycol and 225 g ethanol are added and the mixture is stirred intensively for 15 minutes. The pH value of the solution is adjusted to pH 4.5 with lactic acid. A clear solution is formed that is stable at room temperature and at 4° C. Furthermore this solution can be frozen at −20° C. and results in a clear solution after thawing.

It is concluded that a 0.25% solution of GTN can be prepared using this formula. The long term stability of this solution is excellent as can be seen from the following table:

| Stability at 40° C. | Start | 3 months | 6 months |
| --- | --- | --- | --- |
| GTN assay (HPLC) | 0.252% | 0.252% | 0.245% |
| Stability at 25° C. | | Start | 6 months |
| GTN assay (HPLC) | | 0.252% | 0.246% |

Example 10

5.5 g tyloxapol are dissolved in 84.4 g of purified water. 10.0 g of a 5% solution of GTN in propylene glycol and 0.10 g benzoic acid are added and the mixture is stirred intensively for 15 minutes. The pH value of the solution is adjusted to pH 4.1 with lactic acid. A clear solution is formed that is stable at room temperature and at 4° C. It is concluded that a 0.5% solution of GTN can be prepared using this formula.

Example 11

0.10 g benzoic acid, 6.0 g tyloxapol and 3.0 g poloxamer are dissolved in 50.8 g of purified water. 30.0 g xylitol are added and dissolved by stirring. 10.0 g of a 5 solution of GTN in propylene glycol are added and the mixture is stirred intensively for 15 minutes. The pH value of the solution is adjusted to pH 4.0 with lactic acid. A clear solution is formed that is stable at room temperature and at 4° C. It is concluded that a 0.5% solution of GTN can be prepared using this formula.

Example 12

450.2 g xylitol, 45.0 g tyloxapol and 3.76 g sodium benzoate are dissolved in 929.6 g of purified water. 67.8 g of a 5% solution of GTN in propylene glycol are added and the mixture is stirred intensively for 15 minutes. The pH value is adjusted to pH 4.0 with lactic acid. A clear solution is formed that is stable both at room temperature and at 4° C. The viscosity of this solution is 10 mPa*s.

It is concluded that a 0.22% solution of GTN can be prepared using this formula.

The long term stability of this solution is excellent as can be seen from the following table:

| Stability at 40° C. | Start | 3 months | 6 months |
| --- | --- | --- | --- |
| GTN assay (HPLC) | 0.219% | 0.220% | 0.221% |
| Stability at 25° C. | Start | 3 months | 12 months |
| GTN assay (HPLC) | 0.219% | 0.222% | 0.228% |

Example 13

10.1 g tyloxapol are dissolved in 158.0 g of purified water. 20.0 g of a 5% solution of GTN in ethanol and 11.6 g ethanol are added and mixed. The pH value is adjusted to pH 4.0 with lactic acid. The mixture is stirred intensively for 15 minutes. A clear solution is formed that is stable both at room temperature and at 4° C.

It is concluded that a 0.50% solution of GTN can be prepared using this formula.

Comparative Example 1

30.0 g xylitol are dissolved in 65.5 g of purified water. 4.51 g of a 5% solution of GTN in propylene glycol are added and the mixture is stirred intensively for 15 minutes. Immediately after production droplets of GTN are observed at the bottom of the glass beaker (FIG. 1).

It is concluded that a solution of 0.225% of GTN can not be made in this way.

Comparative Example 2

30.7 g xylitol and 1.0 g tyloxapol are dissolved in 64.5 g of purified water. 4.52 g of a 5% solution of GTN in propylene glycol are added and the mixture is stirred intensively for 15 minutes. Immediately after production the solution is turbid. After three days of storage at room temperature a turbid phase at the bottom of the glass vial and a clear phase above are observed.

It is concluded that 1% tyloxapol is not sufficient to dissolve 0.225% of GTN in this formula.

Comparative Example 3

45.0 g xylitol are dissolved in 49.0 g of purified water. 6.03 g of a 5% solution of GTN in propylene glycol are added and the mixture is stirred intensively for 15 minutes. Immediately after production droplets of GTN are observed at the bottom of the glass beaker (FIG. 2).

It is concluded that a solution of 0.30% of GTN can not be made in this way.

Comparative Example 4

45.1 g xylitol and 1.5 g poloxamer 407 are dissolved in 47.5 g of purified water. 6.01 g of a 5% solution of GTN in propylene glycol are added and the mixture is stirred intensively for 15 minutes. Immediately after production the solution is slightly turbid. After three days of storage at room temperature a turbid phase at the bottom of the glass vial and an opalescent phase above are observed.

It is concluded that 1.5% poloxamer is not sufficient to dissolve 0.30% of GTN in this formula.

Comparative Example 5

35.0 g xylitol are dissolved in 45.0 g of purified water. 5.00 g of a 5% solution of GTN in propylene glycol are dissolved in 15.0 g ethanol. Both solutions are mixed and the mixture is stirred intensively for 15 minutes. Immediately after production the mixture is very turbid, but visually homogeneous. After 3 days of storage at 5° C. droplets of GTN separated from the solution and are observed at the bottom of the glass vial.

Surprisingly the 60-fold excess of ethanol as compared to the amount of GTN is not sufficient to yield a stable solution. It is concluded that a solution of 0.25% of GTN can not be made in this way.

The examples clearly demonstrate that a homogeneous solution is only obtained in the presence of the water soluble polymer. This is also true, if ethanol is used as a preservative. Even if ethanol is present in a concentration of 20 weight percent, this amount of ethanol is not sufficient to solubilise the GTN without a water soluble polymer. For the patient's safety it is required that no phase separation or accumulation of the active substance occurs during storage at lower temperatures (e.g. outside of the house in winter). GTN has a tendency to accumulate at the bottom of the bottle. The dip tube of a spray device would suck this part of the solution first and a patient could be seriously overdosed in this case.

Example 6

This example has been taken from PCT/EP2013/061131 and is included herein to demonstrate the pro-arteriogenic capacities of GTN. Since GTN is the active component of the pharmaceutical composition of the invention, it is concluded that the pharmaceutical composition of the invention is also capable of inducing arteriogenesis.

Pre-Clinical Study

1. Introduction

One important mechanism of arteriogenesis is the induction of shear stress across recruited collateral arteries.

NO plays a fundamental role in this scenario, since it regulates the vasodilatory capability of the artery as well as therapeutic proliferation aspects on the smooth muscle cells of collateral arteries.

Here we evaluated the effects of Nitrolingual Akut® Spray (G. Pohl-Boskamp GmbH & Co.KG, Hohenlockstedt, Germany; U.S. American brand name Nitrolingual® Pumpspray) in a unique non-myocardial infarct arteriogenesis model. Collateral growth in this model is induced via repetitive occlusion of the left anterior descending coronary artery (LAD). Infarct size in these animals was measured as the endpoint at the end of the experiment. Thus, no interference between myocardial infarction and arteriogenesis has weaken the experiment. Moreover we evaluated the effect of acetyl salicylic acid (ASA) in this model of repetitive coronary occlusion as a possible inhibitor of arteriogenesis. We evaluated whether a concomitant application of NO (intermittent use of nitroglycerin) may compensate for this negative effect of ASA.

2. Materials and Methods 1.1. Animal Preparation

Male Sprague-Dawley rats (300 g body weight at study start; n=182) are used for experiments. For surgery (day 0), rats are premedicated (ketamine 50 mg/ml plus xylazine 4 mg/ml intraperitoneal) and intubated. Oral intubation (I4-G polyethylene tubing) is done under direct observation of the vocal cords with an otoscope. General anesthesia is introduced and maintained by isoflurane inhalation (1.0% to 2.0%, with 100% oxygen). Body temperature is controlled at 37° C. by an electric heating table. Surgery is performed using aseptic technique. The animal is initially placed on its dorsal side and cutaneous clips are fixed. With a BioAmp differential amplifier coupled to a PowerLab data acquisition system (AD Instruments) ECG parameters (heart rate) are monitored and recorded during surgery. The heart is exposed by left thoracotomy. A mini-pneumatic snare occluder (see the Mini-Pneumatic Snare Occluder section for details) is implanted around the mid to proximal left anterior descending coronary artery (LAD). Confirmation that the occluder is functional, i.e., producing myocardial ischemia, is determined initially by observation of blanching and hypokinesis of the left ventricle (LV) and by observation of the electrocardiogram (ST elevation) during inflation. Rats are randomly divided into 4 therapeutic modules:

Module 1: Sham Operation
Module 2: NO intermittent (nitroglycerin)
Module 3: NO continuous (retard preparation of isosorbide dinitrate)
Module 4: NO intermittent plus ASA After instrumentation and measurements, the chest is closed under positive end-expiratory pressure, and the thoracic cavity is evacuated of air. The occluders are tunneled subcutaneously and exteriorized between the scapulae. These catheters are protected by a stainless steel spring coil connected to a ring that is secured subcutaneously between the scapulae. After the surgery, analgesic (buprenorphine 0.05 mg/kg SC) and antibiotic (enrofloxacin 10 mg/kg SC) are administered. Rats are observed in a recovery cage for 2 hours and then transferred to the animal care facility where they are continuously monitored by technicians. Postoperatively, buprenorphine (0.5 mg/kg SC) is given for pain twice a day for 8 resp. 13 days. On the third day after the surgery (day 3), ischemic protocol is started. After 5 resp. 10 days (only in module 1A and 2A) of the experimental protocol (day 8 resp. day 13), the rats are anesthetized, and the chest is opened by mid thoracotomy. In the micro-CT group, the hearts are immediately excised. For the final infarct size detection the LAD is permanently occluded (final permanent occlusion, FPO) and infarct size is measured via TTC staining.

1.2. Mini-Pneumatic Snare Occluder for Rat Heart

A mini-pneumatic snare occluder is used consisting of a mini-balloon, sheath tubing, suture, and catheter. The balloon (7 mm long) is made of soft latex membrane and is sufficiently pliable to give negligible physical force on the coronary vessels during balloon deflation. The balloon is mounted within an umbrella sheath (3.2 or 4.8 mm in diameter, 12 mm in length; protects the balloon from fibrous infiltration). Prolene (5-0) is passed around the LAD and attached to the sheath, securing the occluder to the heart, so that myocardial ischemia is produced by balloon inflation. Inflation volume is small (0.2 to 0.25 mL air), but occlusion occurs by 2 physical actions: "crimping" the LAD toward upward/outside and compressing the LAD by the inflated balloon/sheath. The balloon is connected to a catheter (PE-50) that is exteriorized. Balloon inflation and deflation are controlled from outside the rat cage.

1.3. Measurements of ECG Parameters

In all four modules (1-4) at the beginning (day 3) and the end (day 8 resp. day 13) of the experimental protocol (RIP) the coronary occlusion is performed for 40 seconds (equivalent to an occlusion in the RIP; see page 6) and during FPO for 90 minutes (day 8 resp. day 13) ECG parameters are measured to examine the heart rate and ST elevation. Furthermore, the occurring arrhythmias during FPO are determined. According to Lown's classification, every animal shows a certain grade. The higher a grade, the more severe arrhythmias are. To illustrate the mean severity of an entire group more descriptive, a VPB score is ascertained. For that, every Lown grade refers to a particular factor (grade 0=factor 0; grade I=factor 1; grade II=factor 2; grade IIIa=factor 3; grade IIIb=factor 4; grade VIa=factor 5; grade VIb=factor 6 and grade V=factor 7). Every group has a different percentage of animals presenting each grade. The percentage of the respective grades are multiplied with the appropriate factor leading to individual results which are then summed up to the VPB score of the whole group. Consequently, a group of animals with higher Lown grades has a correlatively high VPB score.

1.4. Coronary Microvascular Imaging with Micro-CT

In addition Micro-CT is used as a further endpoint to image collaterals. One group of rats (3 rats of each group in each module; total of 36 rats) is prepared for coronary vascular visualization via micro-CT. The coronary circulation is filled with contrast medium (yellow microfil) by modification of the methodology for micro-CT study in the rats. The viscosity of the contrast medium enables filling up to coronary arteriolar level with no or minimal filling of capillaries. The excised heart is immediately cannulated by an aortic cannula, and coronary circulation is perfused retrogradely at 85 mm Hg. A perfusate (25° C. to 27° C. saline with 2% procaine) is used to avoid myocardial metabolic contraction and maximally dilate the coronary vasculature. Polyethylene tubing is inserted into the LV via a left appendage through the mitral valve to unload the LV. Warmed contrast medium (42° C.) is injected at a pressure of 85 mmHg for 3 minutes while perfusion pressure is monitored. The heart is cooled by immersion into cold saline (0° C. to 4° C.) until the (yellow microfil) solidified. Then, the heart is removed and fixed in 4% paraformaldehyde solution (4° C.) overnight. Whole hearts are used for micro-CT imaging of coronary collateral growth. The coronary vasculature is visualized with micro-CT. In brief, the whole heart is scanned in 1° increments around 360° about its apex-to-base longitudinal axis. The spatial resolution selected in the present study has an 18*18*18 m3 voxel size to focus on the size of collateral vessels and to minimize the signals from smaller vessels. Finally, CT data are reconstructed as 3D images. The main purpose of these images is to establish the presence or absence of arterial-arterial anastomotic connections. Collateral vessels, i.e., arterial-arterial anastomotic connections, are measured by independent observers for the groups. Collateral arterial network morphology is analyzed with Amira 5.2.2 software (Visage Imaging, Berlin, Germany).

1.5. Experimental Protocol

The repetitive ischemia protocol (RIP) is introduced by automatised inflation of the occluder using the following protocol: 40 seconds of occlusion every 20 minutes for 2 hours 20 minutes, followed by a period of "rest" (deflation) for 5 hours 40 minutes. This 8-hour set is repeated 3 times a day for 5 resp. 10 days (only in module 1A and 2A). The LAD is occluded automatically by remote inflation or deflation through the catheter. In sham rats (see module 1), the balloon is implanted, but RIP is not applied. Rats under RI protocol are randomly divided into the three modules 2, 3 and 4.

1.6. Infarct Size Detection

Infarct size is detected by TTC staining after final permanent occlusion. After 5 resp.

10 days (only in module 1A and 2A) of the experimental protocol, the occluder is inflated permanently for 90 minutes. Infarct size is measured by TTC staining (n=10/group). Therefore rats are anaesthesized and undergo again the ECG recording to confirm the occlusion (ST elevation) and to calculate ECG parameters and the numbers of arrhythmias. In animals without collaterals, coronary occlusion causes deterioration of systemic hemodynamics and arrhythmias, including premature ventricular contractions, ventricular tachycardia, and ventricular fibrillation; in animals with well developed collaterals, no such adverse effects are noted. The ECG parameters were recorded and analysed using a computerized program (Lab chart 7).

The chest is opened by mid thoracotomy. The heart is immediately excised and sectioned from apex to base in 2-mm-thick transverse slices parallel to the atrioventricular groove. Slices are incubated with 0.09 mol/L sodium phosphate buffer containing 1.0% triphenyl tetrazolium chloride (TTC) and 8% dextran for 20 min. at 37° C. Slices are fixed in 10% formaldehyde and then photographed with a digital camera mounted on a stereomicroscope. The infarcted size is quantified using a computerized planmetric program (Adobe Photoshop). The infarcted area is indentified as the TTC-negative tissue and is expressed as a percentage of the area of the left ventricle (LV).

1.7. Details Regarding Testing Compounds

ASA Merck Chemicals

NO intermittent (NTG) nitroglycerin solution; Nitrolingual Akut® Spray, G. Pohl-Boskamp GmbH & Co. KG, Hohenlockstedt, Germany NO continuous (ISDN retard) isosorbide dinitrate retard pellets; Nitrosorbon® retard; G. Pohl-Boskamp GmbH & Co. KG, Hohenlockstedt, Germany Carrier Compound for NO Intermittent (NTG-Placebo) placebo solution of Nitrolingual Akut® Spray, Pohl-Boskamp GmbH & Co. KG, Hohenlockstedt, Germany NO Continuous Carrier Compound (ISDN-Placebo) neutral pellets of Nitrosorbon® retard; G. Pohl-Boskamp GmbH & Co. KG, Hohenlockstedt, Germany Control buffer PBS (phosphate buffered saline)

1.8. Route, Timepoint and Concentration of Delivery to Animals

All medication (ASA and NTG and ISDN retard) is given upfront to a following occlusion time of the device. The control buffer (PBS) is given in the same way prior to the first two occlusions.

NO Intermittent (NTG)

A new test solution is prepared every morning at eight o'clock. The solution is taken from the vials via syringes.

NO intermittent (NTG) is given twice a day with a time interval of 8 hours.

Due to the chronic instrumentation of the rats and to avoid further stress, NTG is given via buccal application. 50 µl of the daily prepared test solution containing 17.37 µg nitroglycerin (equivalent to a human dose of 0.8 mg, as calculated by the formula dosis/animal [mg]=metabolic body weight [kg0,75]*human dosis [mg/kg]*recalculation factor [kg/kg0,75] according to Loscher, W., Ungemach, F.R., Kroker, R., 1998, Blackwell Science, 3rd edition) is administered per buccal application in module 1, 2 and 4. The time point of application is directly upfront to balloon inflation at 9 a.m. and 5 p.m., thus with maximal effects on recruited collateral arteries.

This concentration is taken from the above mentioned reaction vials right before administration.

Carrier compound solution served as a stock solution for the preparation of the test solution.

Carrier Compound for NO Intermittent (NTG-Placebo)

Carrier compound is administered in a way identical to NO intermittent.

NO Continuous (ISDN Retard)

The medication for prolonged NO delivery (retard preparation isosorbide dinitrate=long-acting nitrate ISDN) is delivered as retarded pellets 1× per day.

For the retard preparation ISDN in a dosage of 2.6 mg ISDN/rat is chosen. Therefore 13 mg pellets are suspended in 0.5 ml drinking water and are applied via gavage at 9 a.m. every morning (equivalent of a human dose of 2 mg/kg/bw).

NO Continuous Carrier Compound (ISDN-Placebo)

Carrier compound is administered in a way identical to NO continuous.

No Intermittent Plus ASA (Acetylsalicylic Acid)

Every morning at 9.30 a.m. 2.22 mg ASA per rat is given dissolved in 0.5 ml drinking water via gavage directly into the stomach.

The ASA concentration of 2.22 mg ASA per rat (6.34 mg/kg bw) correlates with the human dosage of 100 mg/day.

1.9. Animals and Groups 10 rats per groups (FPO=final permanent occlusion to induce infarcts) Group d: 3 additional animals are treated with the same medications and ligation scheme like the corresponding groups a, b and c, but without FPO. These 9 animals per module are used for micro CT images.

Module 1: Sham Operation (without the RIP):

A. Control buffer (phosphate buffered saline PBS) with functional FPO for infarct size detection n=20
 1. n=10: "5 DAYS SHAM PBS"
 2. n=10 "10 DAYS SHAM PBS"
B. Carrier compound without NO plus functional FPO for infarct size detection
 n=10: "5 DAYS SHAM NTG-PLACEBO"
C. NTG with functional FPO for infarct size detection
 n=10: "5 DAYS SHAM NTG"
D. A1.) n=3 A2.) n=3 B) n=3 C) n=3 for micro CT images
 n=12
 total: n=52

Module 2: NO Intermittent:

A. intermittent control buffer with functional FPO for infarct size detection
 n=20
 1. n=10: "5 DAYS RIP PBS"
 2. n=10: "10 DAYS RIP PBS"

B. intermittent Carrier compound plus functional FPO for infarct size detection
   n=10: "5 DAYS RIP NTG-PLACEBO"
C. Intermittent NTG with functional FPO for infarct size detection
   n=10: "5 DAYS RIP NTG"
D. A1.) n=3 A2.) n=3 B) n=3 C) n=3 for micro CT images
   n=12
   total: n=52
Module 3: NO Continuous:
A. Continuous Control buffer (drinking water) with functional FPO for infarct size detection (n=10): "5 DAYS RIP DW"
B. Continuous Carrier compound plus functional FPO for infarct size detection n=10: "5 DAYS RIP ISDN-PLACEBO"
C. Continuous NO functional FPO for infarct size detection
   n=10: "5 DAYS RIP ISDN"
D. A.) n=3 B.) n=3 C.) n=3 for micro CT images
   n=9
   total: n=(39)
Module 4: NO Intermittent Plus ASA:
A. Intermittent Control buffer plus ASA with functional FPO for infarct size detection n=10: "5 DAYS RIP PBS+ASA"
B. Intermittent NO Carrier compound plus ASA plus functional FPO for infarct size detection n=10: "5 DAYS RIP NTG-PLACEBO+ASA"
C. Intermittent NTG plus ASA functional FPO for infarct size detection
   n=10: "5 DAYS RIP NTG+ASA"
D. A.) n=3 B.) n=3 C.) n=3 for micro CT images
   n=9
   total: n=39

2. Statistical Analysis

All data are given as mean±SD. Graphics are shown as mean±SEM.

Results obtained by measuring ST segment elevation, infarct size and vessel diameters are analysed for statistical significance by using the SPSS 20 software package (IBM SPSS Statistics, NY, USA). ANOVA with a false discovery rate, FDR, correction is used. p values are adjusted for multiple testing using a FDR procedure to achieve an experiment-wide significance of p 0.05. FDR takes into account the number of null hypotheses rejected and has been shown to increase statistical power as compared to Bonferroni correction.

3. Results 3.1 Final Permanent Occlusion

LAD occlusion allowed a prospective study of the function of collateral vessels. Such vessels can protect myocardial tissue at risk of ischemia after coronary occlusion.

At the end of the RI protocol the permanent LAD occlusion is performed in one subgroup of all groups and ECG parameters to examine ST segment elevation and ventricular arrhythmias are measured. After 90 minutes of permanent occlusion the infarcted area is determined.

3.2 ECG Analysis

Electrocardiographic manifestations of ischemia initiated by LAD occlusion are less pronounced when collateral vessels are present.

3.3 ST Segment Elevation

During LAD occlusion there is an inverse correlation between the magnitude of ST segment elevation and the extent of the collateral supply.

Collateral function is an important determinant of the direction of ST segment response to ischemia during acute coronary occlusion. Reversible ST segment elevation during acute LAD occlusion is related to inadequate collateral arterial function. In patients with reversible ST segment depression, coronary collateral function appears to be better and, as a consequence, shows less ischemia results.

During the 90 minutes occlusion the ST segment elevation in the "10 DAYS SHAM PBS" is significantly higher compared to the "10 DAYS RIP PBS" group (10 DAYS SHAM, n=7: 0.124±0.039 mV; 10 DAYS RIP, n=7: 0.055±0.033 mV). In contrast, ST segment elevation in the "5 DAYS SHAM PBS" is similar to the "5 DAYS RIP PBS" group (5 DAYS SHAM, n=8: 0.134±0.034 mV; 5 DAYS RIP, n=8: 0.104±0.016 mV) (FIGS. 3 and 4).

Module 1: Sham Operation (without the RIP)

There is no significance between the three SHAM-groups (5 DAYS SHAM PBS, n=8: 0.134±0.034 mV; 5 DAYS SHAM NTG-PLACEBO, n=6: 0.131±0.043 mV; 5 DAYS SHAM NTG, n=7: 0.124±0.058 mV) (FIGS. 5 and 6).

Module 2: NO Intermittent (NTG)

In the NTG group ("5 DAYS RIP NTG") ST elevation is significantly decreased compared to the PBS group (5 DAYS RIP PBS, n=8: 0.104±0.016 mV; 5 DAYS RIP NTG, n=7: 0.052±0.030 mV). There is no significance between the PBS and NTG-PLACEBO-group (5 DAYS NTG-PLACEBO: n=6; 0.096±0.061 mV) (FIGS. 7 and 8).

Module 3: NO Continuous (ISDN Retard)

ST segment elevation in the ISDN group ("5 DAYS RIP ISDN") is decreased compared to the PBS group (5 DAYS RIP PBS, n=8: 0.104±0.016 mV; 5 DAYS RIP ISDN, n=7: 0.062±0.027 mV), but there is no significance as well as between the PBS and ISDN-PLACEBO-group (5 DAYS ISDN-PLACEBO, n=7: 0.110±0.069 mV) (FIGS. 9 and 10).

Module 4: NO Intermittent Plus ASA

ST segment elevation in the group treated with PBS and ASA is higher compared to the PBS control group (5 DAYS RIP ASA+PBS, n=7: 0.138±0.098 mV; 5 DAYS RIP PBS, n=8; 0.104±0.016 mV), but there is no significance as well as between the ASA+NTG-PLACEBO-group (5 DAYS RIP ASA+NTG-PLACEBO, n=6: 0.144±0.091 mV). In the ASA+NTG-group ST elevation is decreased compared to the group treated with ASA and PBS (5 DAYS RIP NTG+ASA, n=7: 0.088±0.071 mV) (FIGS. 11 and 12).

3.4. Ventricular Arrhythmias

The importance of ventricular premature beats (VPBs) results from their possible association with an increased risk for cardiac sudden death. VPBs were stratified according to the Lown classification. A high Lown grade has been shown to predict mortality after acute myocardial infarction.

Grade 0: no ventricular ectopic beats
Grade I: occasional, isolated VPB
Grade II: frequent VPB (>1/min or 30/h)
Grade III: multiform VPB
  (a) VPB
  (b) Bigenimus
Grade IV: repetitive VPB
  (a) Couplets
  (b) Salvos
Grade V: Early VPB Module 1: Sham Operation (without the RIP)

In the "5 DAYS SHAM PBS" group 87.5% of the rats have class IVb arrhythmias and 12.5% class IVa. In the "5 DAYS SHAM NTG-PLACEBO" group 83.3% have IVb arrhythmias and 16.7% class IVa and in the "5 DAYS SHAM NTG" group 85.7% have IVb arrhythmias and 14.3% class IIIa arrhythmias (FIG. 13).

Module 2: NO Intermittent (NTG)

In the "5 DAYS RIP PBS" group, 75.0% of the rats have class IVb arrhythmias, 12.5% IVa and 12.5% class 0.

Regarding the "5 DAYS RIP NTG-PLACEBO" group, 50.0% of the rats showed class IVb arrhythmias, 16.7% IVa, 16.7% class IIIb and 16.7% class 0 arrhythmias. Interestingly, the "5 DAYS RIP NTG" group shows 42.9% class IVb arrhythmias and 57.1% class 0 arrhythmias (FIG. 14).

Module 3: NO Continuous (ISDN Retard)

In the "5 DAYS ISDN-PLACEBO" group, 57.1% of the rats have class IVb arrhythmias, 14.3% class IVa and 28.6% class IIIb. The "5 DAYS RIP ISDN" group shows less severe arrhythmias with 57.1% class IVb, 28.6% class IIIb and 14.3% class 0 arrhythmias (FIG. 15).

Module 4: NO Intermittent Plus ASA

In the "5 DAYS RIP ASA+PBS" group, in the group treated with ASS+NTG-PLACEBO and in the "5 DAYS RIP ASS+NTG" group 83.3% of the rats posses class IVb arrhythmias and 16.7% class IIIa (FIG. 16).

Regarding the percentage of each Lown grade of every group, a VBP score can be ascertained. The more animals show a higher grade, the higher is the VBP score (FIG. 17).

FIG. 19: VPB-Score

TABLE 1

VPB-Score

| group | VPB-Score |
|---|---|
| Module 1 | |
| SHAM PBS | 5.88 |
| SHAM NTG-PLACEBO | 5.83 |
| SHAM NTG | 5.71 |
| Module 2 | |
| RIP PBS | 5.13 |
| RIP NTG-PLACEBO | 4.50 |
| RIP NTG | 2.57 |
| Module 3 | |
| RIP PBS | 5.13 |
| RIP ISDN-PLACEBO | 5.29 |
| RIP ISDN | 4.57 |
| Module 4 | |
| RIP ASA + PBS | 5.50 |
| RIP ASA + NTG-PLACEBO | 5.50 |
| RIP ASA + NTG | 5.50 |

3.5. Infarct Size

After 90 minutes of LAD occlusion and 20 minutes reperfusion, infarct size was analyzed.

The "10 DAYS RIP PBS" group has a significantly smaller infarct area compared to the "10 DAYS SHAM PBS" group (10 DAYS RIP PBS, n=6: 6.57±3.26%; 10 DAYS SHAM PBS, n=7: 13.71±6.04%). There is no significance between both 5 DAYS groups (5 DAYS SHAM PBS, n=8: 13.36±5.22%; 5 DAYS RIP PBS, n=8: 11.05±5.12%) (FIG. 18).

Module 1: Sham Operation (without the RIP)

There is no significance between the three SHAM-groups (5 DAYS SHAM PBS, n=8: 13.36±5.22%; 5 DAYS SHAM NTG-PLACEBO, n=6: 14.21±5.79%; 5 DAYS SHAM NTG, n=7: 14.09±5.18%) (FIG. 19).

Module 2: NO Intermittent (NTG)

Compared to the "5 DAYS RIP PBS", a significantly smaller infarct area is observed in the "5 DAYS RIP NTG" group (5 DAYS RIP PBS, n=8: 11.05±5.12%; 5 DAYS RIP NTG, n=7: 3.61±2.08%). There is no significance between the PBS and NTG-PLACEBO-group (5 DAYS NTG-PLACEBO: n=6; 9.80±6.79%) (FIG. 20).

Module 3: NO Continuous (ISDN Retard)

The infarct size in the ISDN group ("5 DAYS RIP ISDN") is smaller compared to the PBS group (5 DAYS RIP PBS, n=8: 11.05±5.12%; 5 DAYS RIP ISDN, n=7: 7.59±4.38%), as well as the ISDN-PLACEBO-group (5 DAYS ISDN-PLACEBO, n=6: 9.97±3.65%) (FIG. 21).

Module 4: NO Intermittent Plus ASA

The infarct size in the group treated with ASA ("5 DAYS ASA+PBS") is minimally increased compared to the PBS control group (5 DAYS RIP ASA+PBS, n=6: 12.51±3.05%; 5 DAYS RIP PBS, n=8; 11.05±5.12%), as well as the ASA+NTG-PLACEBO-group (5 DAYS RIP ASA+NTG-PLACEBO, n=6: 13.92±1.71%). There is no difference between the ASA+NTG-group and the group treated with ASA and PBS (FIG. 22). However, the infarct area in the NTG group is significantly smaller compared to the ASA+NTG group (5 DAYS RIP NTG, n=7: 3.61±2.08%; 5 DAYS RIP NTG+ASS, n=6: 13.00±3.82%) (FIG. 23).

3.6. Coronary Microvascular Imaging with Micro-CT

Collateral arteries are pre-existent vessels running parallel to a major artery. In case the major artery is occluded, even for a short period of time (40 sec during this RIP), collaterals assume the blood supply. As a result, collateral arteries in this area (ROI, region of interest) start to grow in length (clearly visible by the cork screw pattern) and most notably in their diameter. So we measured the diameter of the collaterals in the ROI.

Module 1: Sham Operation (without the RIP)

There is no significance between the three SHAM-groups (5 DAYS SHAM PBS, n=3: 82.7±3.7 µm; 5 DAYS SHAM NTG-PLACEBO, n=3: 89.6 µm±10.6 µm; 5 DAYS SHAM NTG, n=3: 86.8±9.0 µm) (FIGS. 24 and 28).

Module 2: NO Intermittent (NTG)

Compared to the "5 DAYS RIP PBS", the diameters of the collaterals in the ROI in the "5 DAYS RIP NTG" group are significantly increased (5 DAYS RIP PBS, n=3: 129.8±6.9 µm; 5 DAYS RIP NTG, n=3: 158.4±9.2 µm). There is no difference between the PBS and NTG-PLACEBO-group (5 DAYS NTG-PLACEBO: n=3; 127.0±12.1 µm) (FIGS. 25 and 28).

Module 3: NO Continuous (ISDN Retard)

The diameter of the collaterals in the ISDN group ("5 DAYS RIP ISDN") are enhanced compared to the PBS group (5 DAYS RIP PBS, n=3: 129.8±6.9 µm; 5 DAYS RIP ISDN, n=3: 148.2±11.3 µm), as well as compared to the ISDN-PLACEBO group (5 DAYS ISDN-PLACEBO, n=3: 133.0±11.5 µm) (FIGS. 26 and 28).

Module 4: NO Intermittent Plus ASA

The diameter in the group treated with PBS and ASA are significantly smaller compared to the PBS control group (5 DAYS RIP PBS+ASA, n=3: 102.5±8.0 µm; 5 DAYS RIP PBS, n=3; 129.8±6.9 µm), but there is no significance compared to the ASA+NTG-PLACEBO-group (5 DAYS NTG-PLACEBO+ASA, n=3: 97.1±8.6 µm). In the ASA+NTG-group diameter are significantly increased compared to the group treated with PBS and ASA (5 DAYS RIP ASA+NTG, n=3: 124.4±5.6 µm) (FIGS. 27 and 28).

4. Conclusion

We examined the groups "10 DAYS SHAM PBS" and "5 DAYS SHAM PBS", each without a RIP (repetitive ischemic protocol) and the groups "10 DAYS RIP PBS" and "5 DAYS RIP PBS", each with a RIP of five and ten days.

Measurement of infarct volume after a 90 minute permanent LAD occlusion (FPO, final permanent occlusion) revealed significantly smaller infarcted areas in the 10 DAYS RIP group than in "10 DAYS SHAM" group. In contrast, after a RIP of five days, no differences became apparent in the SHAM and RIP group.

Moreover, we used ECG parameters for examinations and evaluation for the first time. We found the maximal ST elevation after FPO of the LAD showed no crucial differences between "5 DAYS RIP PBS" and SHAM groups, yet. However, after 10 days ST elevations were significantly decreased in the RIP group.

Aside from ST elevation measurement during FPO, we were able to analyze and evaluate arrhythmias in differentiated way.

Based on these novel insights into the characterization of rat RMI model, we decided to use a 5 day RIP in case of an expected stimulation of arteriogenesis.

The degree of ST elevation enhancement and the infarct volume after a 10 day RIP can be obtained with pro-arteriogenic substances within a 5 day RIP, yet.

This provides additional parameters being able to approve our results of infarct volume measurement.

The intermittent application of NTG solution (twice daily on buccal mucosa) decreased serious arrhythmias of the rat heart during FPO compared to the control group. Additionally, infarct volume is decreased by more than 50% after 90 minutes FPO compared to the control group. This reduction in infarct size is not even obtainable with controls set to a 10 days RIP. Furthermore, a treatment with NTG solution significantly attenuated ST elevation during FPO. On the basis of the μCT analyses, significantly enlarged collateral arteries were measurable.

The treatment of the rats with ISDN retard (once daily intragastrally) also led to decreases in ST elevation during FPO, less arrhythmias and reduced infarct volumes. However, these improvements of infarct parameters are less distinct compared with NTG treatment. Moreover, they did not show any significance.

Compared to controls, the treatment with ASA showed an impairment of ECG parameters and an increase of infarct volumes due to impaired collateral growth. These negative effects of ASA on arteriogenesis are already known. Interestingly, they can be partly abolished through an additional NTG treatment (twice daily on buccal mucosa). Thus, collateral diameters were enlarged in the ROI and ECG parameters were enhanced. Nevertheless, infarct volumes after FPO showed no reduction.

The SHAM groups did not differ among each other.

Further on, there were no differences measured between the Placebo groups and their corresponding control groups.

In conclusion, the presented results indicate that an intermittent treatment with NTG solution decreases the size of an experimentally induced myocardial infarct.

In addition, effects on cardiac rhythm may ameliorate. These insights are of outstanding relevance for clinical aspects.

Example 7

A preferred formulation prepared in accordance with the teachings herein will be tested as follows. Patients with a medical history of chronic stable exertional angina due to stable ischemic heart disease (coronary artery disease) will receive a container of an aqueous GTN-containing preparation. The container will be equipped with a pump spray device which delivers a metered dose of 0.4 mg GTN per spray. Patients will sublingually self-administer the specified dose at the onset of an attack of angina pectoris. Patients will document the time lapsed from treatment to relief of the symptoms of angina pectoris, in particular anginal chest pain. It is expected that patients will experience immediate or near-immediate acute relief and return to a symptom-free condition following treatment with the present invention.

Example 8

A preferred formulation prepared in accordance with the teachings herein will be tested as follows. In a placebo-controlled trial patients with a medical history of claudication intermittens due to peripheral artery disease and a maximum walking distance of less than 250 m will receive a container of an aqueous GTN-containing preparation or placebo. The container will be equipped with a pump spray device which delivers a metered dose of 0.15 mg GTN per spray. Patients will sublingually self-administer the specified dose 5 minutes prior a daily walking program of 45-60 minutes. Patients will be monitored at study inclusion (baseline measurement) as well as 8, 12 and 16 weeks after the start of the interventional phase to document their maximum and pain-free walking distances (by means of standard treadmill test) and their quality of life (measured by a quality of life questionnaire) in comparison to their baseline and placebo group. It is expected that patients treated with *verum* will show significant improvements over the placebo patients. GTN-receiving patients will show significantly improved walking impairment with a higher increase in maximum and pain-free walking distances and a higher quality of life due to GTN-induced higher increased collateral circulation by means of arteriogenesis.

The invention claimed is:
1. An aqueous pharmaceutical preparation comprising:
   (a) a first component comprising 0.15 to 3 weight percent of glyceryl trinitrate,
   (b) a second component comprising 40 to 95 weight percent water,
   (c) a third component comprising 1 to 10 weight percent of at least one non-ionic water soluble polymer; and,
   (d) a fourth component comprising 5 to 20 weight percent of ethanol; wherein the non-ionic water soluble polymer is selected from the group of non-ionic polymers consisting of: tyloxapol, poloxamer, and a mixture of tyloxapol and poloxamer.
2. An aqueous pharmaceutical preparation comprising:
   (a) a first component comprising 0.15 to 3 weight percent of glyceryl trinitrate,
   (b) a second component comprising 40 to 95 weight percent water, and;
   (c) a third component comprising 2 to 10 weight percent of at least one non-ionic water soluble polymer, wherein the non-ionic water soluble polymer is selected from the group of non-ionic polymers consisting of: tyloxapol, poloxamer, and a mixture of tyloxapol and poloxamer.
3. The aqueous pharmaceutical preparation according to claim 1 or 2 further comprising at least one additive selected from the group consisting of: a preservative, a taste component, a flavor component, a sweetener, an acid, a base, and a buffering substance.
4. The aqueous pharmaceutical preparation according to claim 3 wherein xylitol is a taste component.
5. The aqueous pharmaceutical preparation according to 3 wherein a buffering substance is present at about 0.1 to 1 weight percent.
6. The aqueous pharmaceutical preparation according to claim 1 or 2 wherein the viscosity of the preparation is not more than 50 mPa*s, wherein viscosity is measured at 20° C. with a rotational viscosimeter at a shear rate of 1800/s.

7. The aqueous pharmaceutical preparation according to claim 1 or 2 wherein the viscosity of the preparation is not more than 40 mPa*s, wherein viscosity is measured at 20 ° C. with a rotational viscosimeter at a shear rate of 1800/s.

8. The aqueous pharmaceutical preparation according to claim 1 or 2 wherein the viscosity of the preparation is not more than 30 mPa*s, wherein viscosity is measured at 20 ° C. with a rotational viscosimeter at a shear rate of 1800/s.

9. The aqueous pharmaceutical preparation of claim 1 or 2 wherein the preparation is in the form of a spray.

* * * * *